(12) United States Patent
Trepagnier et al.

(10) Patent No.: US 11,505,820 B2
(45) Date of Patent: Nov. 22, 2022

(54) METHODS FOR NUCLEIC ACID DETECTION

(71) Applicant: ULTIMA GENOMICS, INC., Newark, CA (US)

(72) Inventors: Eliane Trepagnier, Fremont, CA (US); Mark Pratt, Bozeman, MT (US); Theo Nikiforov, Carlsbad, CA (US); Gilad Almogy, Palo Alto, CA (US)

(73) Assignee: ULTIMA GENOMICS, INC., Newark, CA (US)

( * ) Notice: Subject to any disclaimer, the term of this patent is extended or adjusted under 35 U.S.C. 154(b) by 123 days.

(21) Appl. No.: 16/936,619

(22) Filed: Jul. 23, 2020

(65) Prior Publication Data
US 2021/0040543 A1 Feb. 11, 2021

Related U.S. Application Data

(63) Continuation of application No. PCT/US2019/016699, filed on Feb. 5, 2019.

(60) Provisional application No. 62/627,074, filed on Feb. 6, 2018.

(51) Int. Cl.
*C12Q 1/6818* (2018.01)
*C12Q 1/6869* (2018.01)

(52) U.S. Cl.
CPC ......... *C12Q 1/6818* (2013.01); *C12Q 1/6869* (2013.01)

(58) Field of Classification Search
CPC ............ C12Q 1/6869; C12Q 2525/117; C12Q 2565/101; C12Q 2565/518; C12Q 1/6818; G16B 30/20
See application file for complete search history.

(56) References Cited

U.S. PATENT DOCUMENTS

| | | | |
|---|---|---|---|
| 6,103,474 A | 8/2000 | Dellinger et al. | |
| 2003/0134808 A1* | 7/2003 | Wengel | C07H 21/00 514/44 R |
| 2008/0171665 A1 | 7/2008 | Minor | |
| 2010/0248991 A1* | 9/2010 | Roesler | C12Q 1/6844 506/16 |
| 2016/0019341 A1 | 1/2016 | Harris et al. | |
| 2018/0371537 A1* | 12/2018 | Claes | C12N 15/11 |

FOREIGN PATENT DOCUMENTS

WO  WO-2019156983 A1  8/2019

OTHER PUBLICATIONS

Su et al., "Kinetics of hybridization of interfacial RNA homopolymer studied by thickenss-shear mode acoustic wave sensor", Biosensors & Bioelectronics, vol. 12, No. 3, pp. 161-173. (Year: 1997).*
PCT/US19/16699 International Search Report dated Apr. 11, 2019.

* cited by examiner

*Primary Examiner* — Young J Kim
(74) *Attorney, Agent, or Firm* — Wilson Sonsini Goodrich & Rosati

(57) ABSTRACT

The present disclosure provides methods and systems for sequencing nucleic acid molecules in a manner that enables higher sequencing accuracy. Methods and systems provided herein may enable sequences that may have low-accuracy reads, such as homopolymer sequences or other repeating sequences, to be determined at a higher accuracy and efficiency.

20 Claims, 10 Drawing Sheets
Specification includes a Sequence Listing.

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
aaaaaaaaaa aaaaa                                                    15
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gactttttt tttttttggg t                                               21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 gactttttt tttttttttt ggt                                             23

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 gactttttt tttagc                                                     16

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (12)..(14)
<223> OTHER INFORMATION: a, c, t, g, unknown or other

<400> SEQUENCE: 5
nnnnaaaaaa annn                                                      14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (12)..(14)
<223> OTHER INFORMATION: a, c, t, g, unknown or other

<400> SEQUENCE: 6

```
nnnaaaaaaa annn                                                    14
```

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 7

```
naaaaaaaaa aaan                                                    14
```

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (14)..(16)
<223> OTHER INFORMATION: a, c, t, g, unknown or other

<400> SEQUENCE: 8

```
nnnaaaaaaa aaannn                                                  16
```

METHODS FOR NUCLEIC ACID DETECTION

CROSS REFERENCE

This application is a continuation of International Application No. PCT/US2019/016699, filed Feb. 5, 2019, which claims the benefit of U.S. Provisional Application No. 62/627,074, filed Feb. 6, 2018, which application is entirely incorporated herein by reference.

SEQUENCE LISTING

The instant application contains a Sequence Listing which has been submitted electronically in ASCII format and is hereby incorporated by reference in its entirety. Said ASCII copy, created on Feb. 25, 2022, is named 51024_707_301_SL.txt and is 2,802 bytes in size.

BACKGROUND

The detection, quantification and sequencing of nucleic acid molecules (e.g., polynucleotides) may be important for molecular biology and medical applications, such as diagnostics. Genetic testing is useful for a number of diagnostic methods. For example, disorders that are caused by rare genetic alterations (e.g., sequence variants) or changes in epigenetic markers, such as cancer and partial or complete aneuploidy, may be detected or more accurately characterized with deoxyribonucleic acid (DNA) or ribonucleic acid (RNA) sequence information.

The goal to elucidate the entire human genome has created interest in technologies for rapid nucleic acid (e.g., DNA) sequencing, both for small- and large-scale applications. Some important parameters are sequencing speed, sequencing accuracy, length of sequence that can be read during a single sequencing run, and amount of nucleic acid template required to generate sequencing information. Large scale genome projects may be too expensive to be practicable for analyzing a large number of subjects (e.g., patients). Furthermore, as knowledge of the genetic bases for human diseases increases, the need for accurate, high-throughput DNA sequencing that is affordable will also increase. Practical methods for determining the base pair sequences of single molecules of nucleic acids, preferably with high speed, high accuracy and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment of contagious diseases.

SUMMARY

The accuracy of sequencing reads may be lower at certain genomic loci than at other loci, such as where there are homopolymer repeats or other repeats (e.g., dinucleotide repeats, trinucleotide repeats, etc.) in the sequence. Such limitations can render sequencing inefficient or ineffective for use in various applications, such as biological applications aiming to accurately identify various genetic variants.

Recognized herein is the need for methods and systems to accurately sequence a genomic region, such as a homopolymer region or other repeating regions, which may be more difficult to sequence than others.

Methods and systems of the present disclosure advantageously provide for sequencing with improved accuracy. Methods and systems provided herein may determine repeating sequences (e.g., homopolymer, dinucleotide, trinucleotide, etc.) at a higher accuracy and efficiency.

In an aspect, provided is a method for nucleic acid sequencing, comprising: subjecting a first nucleic acid sample of a subject to a first assay to generate a first data set, wherein the first data set comprises a nucleic acid sequence of a target nucleic acid molecule from the first nucleic acid sample; subjecting a second nucleic acid sample of the subject to a second assay to generate a second data set, wherein the second data set comprises a homopolymer sequence of the target nucleic acid molecule, wherein the first assay and the second assay are of different types; and using a programmed computer to combine the first data set and the second data set to generate a combined data set, wherein the combined data set comprises the nucleic acid sequence and the homopolymer sequence, wherein the homopolymer sequence is determined at an accuracy of at least 90%.

In some embodiments, the first nucleic acid sample and the second nucleic acid sample are copies of the target nucleic acid molecule. In some embodiments, the first nucleic acid sample and the second nucleic acid sample are clonal copies of the target nucleic acid molecule.

In some embodiments, the second nucleic acid sample is derived from the first nucleic acid sample. In some embodiments, the second nucleic acid sample is the first nucleic acid sample.

In some embodiments, the first assay and the second assay are performed sequentially. In some embodiments, the first assay is performed subsequent to the second assay. In some embodiments, the second assay is performed subsequent to the first assay.

In some embodiments, the first assay comprises sequencing the first nucleic acid sample. In some embodiments, the first assay comprises subjecting the first nucleic acid sample to sequencing by synthesis.

In some embodiments, the method further comprises generating sequencing reads, and combining the sequencing reads to yield a consensus sequence.

In some embodiments, the second assay comprises array hybridization.

In some embodiments, the second assay comprises using an oligonucleotide probe to hybridize with the target nucleic acid molecule or clonal copies thereof.

In some embodiments, the oligonucleotide probe comprises an observable signal. In some embodiments, the observable signal comprises optical signal, electron signal, or electromagnetic signal. In some embodiments, the oligonucleotide probe is labeled with a reporter moiety. In some embodiments, the reporter moiety comprises one or more dye molecules.

In some embodiments, the oligonucleotide probe comprises at least 5 nucleotides in length. In some embodiments, the oligonucleotide probe comprises at least 10 nucleotides in length. In some embodiments, the oligonucleotide probe comprises at least 15 nucleotides in length. In some embodiments, the oligonucleotide probe comprises at least 20 nucleotides in length.

In some embodiments, the oligonucleotide probe comprises a homopolymer region. In some embodiments, the oligonucleotide probe further comprises a random sequence region.

In some embodiments, the random sequence region comprises at least one nucleotide. In some embodiments, the random sequence region comprises from 1 nucleotide to 10 nucleotides in length.

In some embodiments, the random sequence region is located at the 5' end of the homopolymer region of the oligonucleotide probe. In some embodiments, the random sequence region is located at the 3' end of the homopolymer region of the oligonucleotide probe.

In some embodiments, the oligonucleotide probe comprises at least one modified nucleotide.

In some embodiments, the oligonucleotide probe is a locked nucleic acid.

In some embodiments, the clonal copies of the target nucleic acid molecule is generated by a bead-based method, a solid-state method, or an in-solution DNA nanoball method. In some embodiments, the bead-based method is on-bead emulsion PCR. In some embodiments, the solid-state method is solid-phase bridge amplification or solid-phase template walking.

In some embodiments, the combined data set is a consensus sequence.

In some embodiments, the oligonucleotide probe comprises a first oligonucleotide probe and a second oligonucleotide probe, wherein the first oligonucleotide probe comprises a first homopolymer region and a first random sequence region, and the second oligonucleotide probe comprises a second homopolymer region and a second random sequence region.

In some embodiments, the first oligonucleotide probe and the second oligonucleotide probe are introduced to the second nucleic acid sample separately.

In some embodiments, the first oligonucleotide probe and the second oligonucleotide probe have different total length. In some embodiments, the first oligonucleotide probe and the second oligonucleotide probe have the same total length.

In some embodiments, the first homopolymer region and the second homopolymer region have different length. In some embodiments, the first random sequence region and the second random sequence region have different length.

In some embodiments, the first oligonucleotide probe is a first bracketing probe, and the second oligonucleotide is a second bracketing probe.

In some embodiments, the first bracketing probe and the second bracketing probe is ligated when hybridized to the target nucleic acid molecules or clonal copies thereof.

In some embodiments, the first bracketing probe is separated from the second bracketing probe by a gap region comprising at least one nucleotide.

In some embodiments, the method further comprises filling the gap region by non-strand displacing-extension before ligating.

In some embodiments, the first bracketing probe and the second bracketing probe comprise a fluorescence resonance energy transfer (FRET) dye pair.

In some embodiments, the first assay and the second assay are performed on different sample sets.

In some embodiments, the accuracy is at least 95%. In some embodiments, the accuracy is at least 98%. In some embodiments, the accuracy is at least 99%.

In some embodiments, the second assay comprises determining homopolymer sequences of one or more additional nucleic acid molecules from the second nucleic acid sample.

In another aspect, provided is a method for identifying a sequence of a nucleic acid molecule, comprising: providing the nucleic acid molecule comprising a first homopolymer region, wherein the first homopolymer region has a first length; hybridizing a probe comprising a second homopolymer region having a second length to the first homopolymer region, wherein: (i) a sequence of the first homopolymer region is complementary to a sequence of the second homopolymer region, and (ii) the probe yields an observable signal when the second homopolymer region is hybridized to the first homopolymer region; detecting the observable signal; processing an intensity or relative intensity of the observable signal to determine a match between the first length and the second length; and use the match determined in (d) to identify the sequence of the first homopolymer region.

In some embodiments, the first length is shorter or longer than the second length. In some embodiments, the first length and the second length are the same.

In some embodiments, the first length or second length is up to 50 or 100 nucleotides. In some embodiments, the second length is greater than 5 nucleotides. In some embodiments, the second length is greater than 10 nucleotides. In some embodiments, the second length is greater than 15 nucleotides. In some embodiments, the second length is greater than 20 nucleotides.

In some embodiments, the observable signal is an optical signal, an electronic signal, or an electromagnetic signal. In some embodiments, the observable signal is a fluorescent signal. In some embodiments, the detecting comprises imaging.

In some embodiments, the method further comprises generating a clonal copy of a target nucleic acid molecule and wherein the nucleic acid molecule is the clonal copy of the target nucleic acid molecule. In some embodiments, the clonal copy of the target nucleic acid molecule is generated by a bead-based method, a solid-state method, or an in-solution DNA nanoball method. In some embodiments, the bead-based method is on-bead emulsion PCR. In some embodiments, the solid-state method is solid-phase bridge amplification or solid-phase template walking.

In some embodiments, the clonal copy of the target nucleic acid molecule is attached to a surface. In some embodiments, the surface is a bead surface or a planar surface.

In some embodiments, the probe comprises at least one fluorescent label. In some embodiments, the at least one fluorescent label is labeled at 5' end of the probe. In some embodiments, the at least one fluorescent label is labeled at 3' end of the probe.

In some embodiments, the probe comprises a sequence of poly(dA), poly(dT), poly(dG), poly(dC), poly(rA), poly(U), poly(rG), or poly(rC).

In some embodiments, the probe further comprises a random sequence region. In some embodiments, the random sequence region is located at the 5' end of the probe. In some embodiments, the random sequence region is located at the 3' end of the probe.

In some embodiments, the random sequence region comprises at least one nucleotide. In some embodiments, the random sequence region comprises from 1 nucleotide to 10 nucleotides in length.

In some embodiments, the probe comprises at least one modified nucleotide.

In some embodiments, the at least one modified nucleotide is a locked nucleotide.

In some embodiments, the hybridizing is performed at a first temperature and the detecting is performed at a second temperature, wherein the first temperature is different from the second temperature.

In some embodiments, the second temperature is higher than the first temperature.

In some embodiments, detecting the observable signal is performed in the presence of a nucleic acid hybridization denaturant.

In some embodiments, the method further comprises determining the sequence of the nucleic acid molecule. In some embodiments, determining the sequence of the nucleic acid molecule is achieved by a sequence-by-synthesis method, wherein a synthesized complementary strand of the nucleic acid molecule is generated. In some embodiments, the method further comprises removing the synthesized complementary strand.

In some embodiments, the probe further comprises a first bracketing probe and a second bracketing probe, wherein the first bracketing probe hybridizes with a first segment of the first homopolymer region and the second bracketing probe hybridizes with a second segment of the first homopolymer region.

In some embodiments, the second segment is contiguous to the first segment.

In some embodiments, the second segment is separated from the first segment by a gap region comprising at least one nucleotide.

In some embodiments, the method further comprises ligating the first bracketing probe and the second bracketing probe.

In some embodiments, the method further comprises filling the gap region by non-strand-displacing extension.

In some embodiments, the first bracketing probe comprises a fluorescence resonance energy transfer (FRET) donor and the second bracketing probe comprises a FRET acceptor, thereby generating a FRET signal. In some embodiments, determining the first length is achieved by determining the strength of the FRET signal.

In some embodiments, the method further comprises releasing the probe hybridized to the nucleic acid molecule.

In some embodiments, the method further comprises repeating (b) and (c) at least once with at least one additional probe comprising an additional homopolymer region having a length that is different than the second length, to yield at least one additional observable signal from the at least one additional probe.

In another aspect, provided is a method for determining a sequence of a target nucleic acid molecule, comprising subjecting the target nucleic acid molecule to sequencing-by-synthesis to yield sequence data comprising a first sequence of the target nucleic acid molecule, which sequencing-by-synthesis generates a nucleic acid molecule that is complementary to the target nucleic acid molecule; hybridizing a homopolymer probe to a homopolymer region of the target nucleic acid molecule, wherein the homopolymer probe yields an observable signal that is indicative of a presence of the homopolymer region; detecting the observable signal to identify a homopolymer sequence of the homopolymer region; and combining the sequence data from the first sequence with the homopolymer sequence identified in the detecting to generate a second sequence of the target nucleic acid molecule, which second sequence comprises the first sequence and the homopolymer sequence.

In some embodiments, the subjecting the target nucleic acid molecule to sequencing-by-synthesis is performed subsequent to the hybridizing and the detecting. In some embodiments, the hybridizing and the detecting are performed subsequent to subjecting the target nucleic acid molecule to sequencing-by-synthesis.

In some embodiments, the method further comprises, subsequent to subjecting the target nucleic acid molecule to sequencing-by-synthesis, removing the nucleic acid molecule from the target nucleic acid molecule.

In some embodiments, the method further comprises generating clonal copies of the target nucleic acid molecule in the flow cell.

In some embodiments, the method further comprises determining a sequence of the homopolymer region of the target nucleic acid molecule at an accuracy rate of at least 90%.

In some embodiments, the homopolymer probe comprises greater than 5 nucleotides. In some embodiments, the homopolymer probe comprises greater than 10 nucleotides. In some embodiments, the homopolymer probe comprises greater than 15 nucleotides. In some embodiments, the homopolymer probe comprises greater than 20 nucleotides.

In some embodiments, the observable signal is an optical signal, an electronic signal, or an electromagnetic signal. In some embodiments, the observable signal is a fluorescent signal.

In some embodiments, the detecting comprises imaging.

In some embodiments, the homopolymer probe comprises at least one fluorescent label. In some embodiments, the at least one fluorescent label is labeled at 5' end of the homopolymer probe. In some embodiments, the at least one fluorescent label is labeled at 3' end of the homopolymer probe.

In some embodiments, the homopolymer probe comprises a sequence of poly(dA), poly(dT), poly(dG), poly(dC), poly(rA), poly(U), poly(rG), or poly(rC).

In some embodiments, the homopolymer probe further comprises a random sequence region. In some embodiments, the random sequence region is located at the 5'end of the homopolymer probe. In some embodiments, the random sequence region is located at the 3' end of the homopolymer probe.

In some embodiments, the random sequence region comprises at least one nucleotide. In some embodiments, the random sequence region comprises from 1 nucleotide to 10 nucleotides in length.

In some embodiments, the homopolymer probe comprises at least one modified nucleotide.

In some embodiments, the at least one modified nucleotide is a locked nucleotide.

In some embodiments, the hybridizing is performed at a first temperature and the detecting is performed at a second temperature, wherein the first temperature is different from the second temperature.

In some embodiments, the second temperature is higher than the first temperature.

In some embodiments, the detecting the observable signal is performed in the presence of a nucleic acid hybridization denaturant.

In some embodiments, the homopolymer probe further comprises a first bracketing probe and a second bracketing probe, wherein the first bracketing probe hybridizes with a first segment of the homopolymer region and the second bracketing probe hybridizes with a second segment of the homopolymer region.

In some embodiments, the second segment is contiguous to the first segment.

In some embodiments, the second segment is separated from the first segment by a gap region comprising at least one nucleotide.

In some embodiments, the method further comprises ligating the first bracketing probe and the second bracketing probe.

In some embodiments, the method further comprises filling the gap region by non-strand-displacing extension.

In some embodiments, the first bracketing probe comprises a fluorescence resonance energy transfer (FRET) donor and the second bracketing probe comprises a FRET acceptor, thereby generating a FRET signal.

In some embodiments, the second sequence is a consensus sequence.

In another aspect, provided is a method for determining a sequence of a nucleic acid sample, comprising: using a massively parallel sequencer to identify a first nucleic acid sequence of the nucleic acid sample; using a targeted probe to identify a second nucleic acid sequence of the nucleic acid sample, wherein using the targeted probe is performed separately from using the massively parallel sequencer; and using a programmed computer to generate a consensus sequence from the first nucleic acid sequence and the second nucleic acid sequence at an accuracy of at least 95%.

In some embodiments, the targeted probe is targeted to an array, and wherein using the targeted probe comprises array hybridization.

In some embodiments, the targeted probe is configured to identify a repeated sequence, and the second nucleic acid sequence comprises the repeated sequence. In some embodiments, the repeated sequence is a homopolymer sequence. In some embodiments, the repeated sequence is a dinucleotide repeated sequence. In some embodiments, the repeated sequence is a trinucleotide repeated sequence.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-3C disclose SEQ ID NOS 1-2, 1, 3, 1, and 4, respectively, in order of appearance.

FIG. 5 discloses SEQ ID NOS 5-7, respectively, in order of appearance.

FIG. 6 discloses SEQ ID NOS 8 and 4, respectively, in order of appearance.

FIG. 7 discloses SEQ ID NOS 8 and 4, respectively, in order of appearance.

FIG. 8 discloses SEQ ID NO 4.

DETAILED DESCRIPTION

Figure 1:
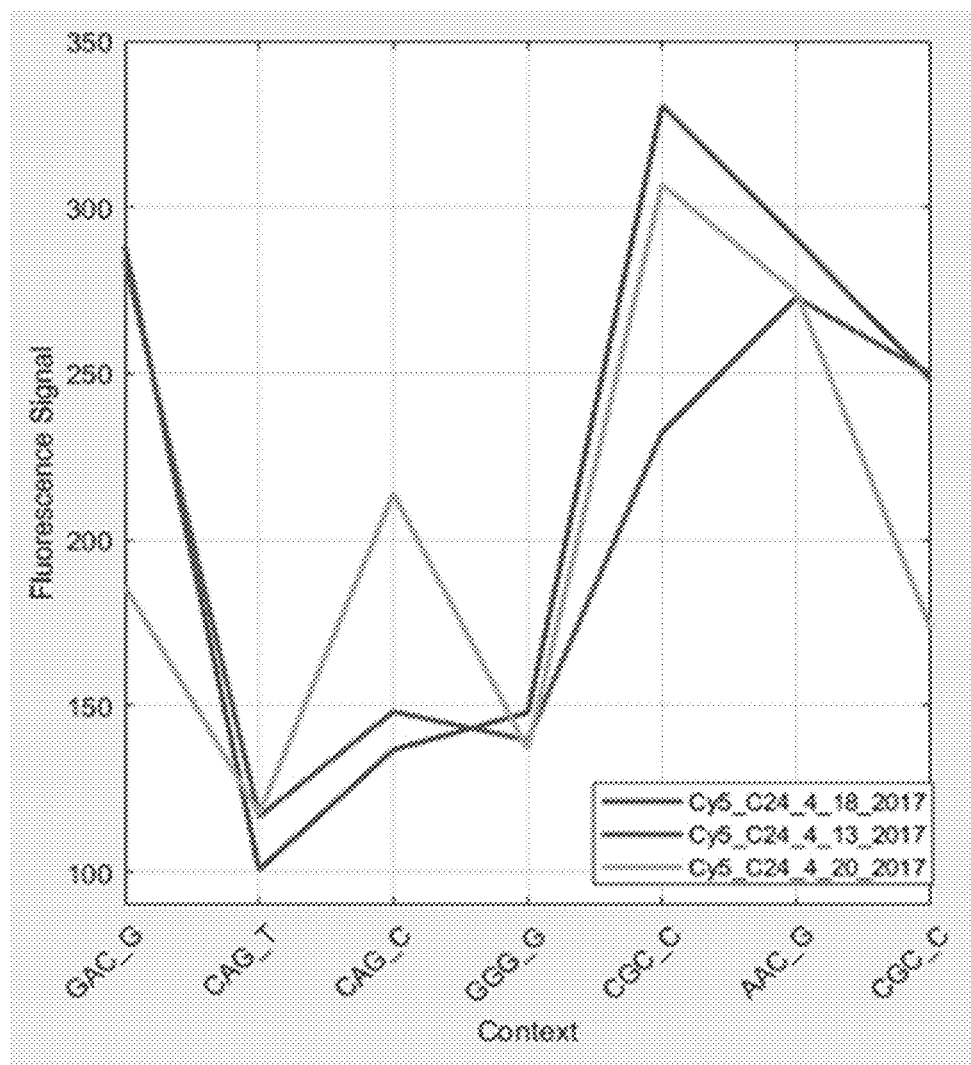
FIG. 1 depicts a context specific assay showing reproducible fluorescent signal variations for different local contexts for a Cy5 labeled dUTP.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sequencing," as used herein, generally refers to a process for generating or identifying a sequence of a biological molecule, such as a nucleic molecule. Such sequence may be a nucleic acid sequence, which may include a sequence of nucleic acid bases. Sequencing may be single molecule sequencing, sequencing by synthesis, sequencing by hybridization, or sequencing by ligation, for example. Sequencing may be performed using template nucleic acid molecules immobilized on a support, such as a flow cell or one or more beads. Sequencing a nucleic acid molecule may generate a "sequencing read" (also "read" herein), which may be data indicative of a sequence of the nucleic acid molecule. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "support" or "substrate," as used herein, generally refers to any solid or semi-solid article on which reagents such as nucleic acid molecules may be immobilized. Nucleic acid molecules may be synthesized, attached, ligated, or otherwise immobilized. Nucleic acid molecules may be immobilized on a substrate by any method including, but not limited to, physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous, and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support). The substrate may be circular and capable of rotating around a rotatable axis.

The term "biological sample," as used herein, generally refers to any sample from a subject. The biological sample can be a fluid or tissue from the subject. The fluid can be blood (e.g., whole blood), saliva, urine, or sweat. The tissue can be from an organ (e.g., liver, lung, or thyroid), or a mass of cellular material, such as, for example, a tumor. The biological sample can be a feces sample, collection of cells (e.g., cheek swab), or hair sample. The biological sample can be a cell-free or cellular sample. Examples of biological samples include nucleic acid molecules, amino acids, polypeptides, proteins, carbohydrates, fats, or viruses. A biological sample may comprise one or more cells. In an example, a biological sample is a nucleic acid sample including one or more nucleic acid molecules, such as deoxyribonucleic acid (DNA) and/or ribonucleic acid (RNA) molecules. The nucleic acid molecules may be included within cells or may be cell-free nucleic acid molecules, such as cell-free DNA molecules or cell-free RNA molecules. The nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like.

The biological sample may be a cell-free sample. The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition, cell-free nucleic acid molecules may be released into bodily fluids from healthy cells.

The term "subject," as used herein, generally refers to an individual from whom a biological sample is obtained. The subject may be a mammal or non-mammal. The subject may be an animal, such as a monkey, dog, cat, bird, or rodent. The subject may be a human. The subject may be a patient. The subject may have or be suspected of having a disease or disorder. The subject may be displaying a symptom of a disease or disorder. The subject may be asymptomatic of a disease or disorder. The subject may be undergoing treatment for a disease or disorder. The subject may not be undergoing treatment for a disease or disorder. Alternatively or in addition, a subject may be known to have previously had a disease or disorder. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The terms "nucleic acid," "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or deoxyribonucleic acids (DNA) or ribonucleotides or ribonucleic acids (RNA), or analogs thereof. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide can comprise a sequence of four natural nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotide(s).

Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes. Nucleotide analogs may be capable of reacting or bonding with detectable moieties for nucleotide detection.

The term "homopolymer," as used herein, generally refers to a polymer or a portion of a polymer comprising identical monomer units. A homopolymer may have a homopolymer sequence. A nucleic acid homopolymer may refer to a polynucleotide or an oligonucleotide comprising consecutive repetitions of a same nucleotide or any nucleotide variants thereof. For example, a homopolymer can be poly (dA), poly(dT), poly(dG), poly(dC), poly(rA), poly(U), poly (rG), or poly(rC). A homopolymer can be of any length. For example, the homopolymer can have a length of at least 2, 3, 4, 5, 10, 20, 30, 40, 50, 100, 200, 300, 400, 500, or more nucleic acid bases. The homopolymer can have from 10 to 500, or 15 to 200, or 20 to 150 nucleic acid bases. The homopolymer can have a length of at most 500, 400, 300, 200, 100, 50, 40, 30, 20, 10, 5, 4, 3, or 2 nucleic acid bases. A molecule, such as a nucleic acid molecule, can include one or more homopolymer portions and one or more non-homopolymer portions. The molecule may be entirely formed of a homopolymer, multiple homopolymers, or a combination of homopolymers and non-homopolymers.

The term "primer," as used herein, generally refers to a polynucleotide which is complementary to a portion of a template nucleic acid molecule. For example, a primer may be complementary to a portion of a strand of a template nucleic acid molecule. A primer may exhibit sequence identity or homology or complementarity to a template nucleic acid molecule. The complementarity or homology or sequence identity between the primer and the template nucleic acid molecule may be limited. The homology or sequence identity or complementarity between the primer and a template nucleic acid molecule may be based on the length of the primer. For example, if the primer length is about 20 nucleotide bases, it may contain 10 or more contiguous nucleotide bases complementary to the template nucleic acid molecule. The length of the primer may be, for example, between 8 and 50 nucleotide bases. In some cases, the length of a primer may be more than 2 nucleotide bases, such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, or more nucleotide bases. In some cases, the length of a primer may be less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or fewer nucleotide bases.

The term "primer extension reaction," as used herein, generally refers to binding of a primer to a strand of a template nucleic acid molecule, followed by elongation of the primer. It may also include denaturing of a double-stranded nucleic acid molecule and the binding of a primer to either one or both denatured strands of the double-stranded nucleic acid molecule, followed by elongation of one or more primers. Primer extension reactions may be used to incorporate nucleotides or nucleotide analogs to a primer in template-directed fashion by using enzymes (e.g., polymerizing enzymes).

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C. C. PNAS, 1989, 86, 4076-4080 and U.S. Pat. Nos. 5,409,811 and 5,674,716, each of which is herein incorporated by reference in its entirety.

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference). The enhanced signal-to-noise ratio provided by clonal amplification more than outweighs the disadvantages of the cyclic sequencing requirement.

The term "polymerase," as used herein, generally refers to any enzyme capable of catalyzing a polymerization reaction. The polymerase used herein can have strand displacement activity or non-strand displacement activity. Examples of polymerases include, without limitation, a nucleic acid polymerase. The polymerase can be naturally occurring or synthesized. In some cases, a polymerase has relatively high processivity. An example polymerase is a Φ29 DNA polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfu-turbo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such as for example, Sequenase DNA polymerase (ThermoFisher).

A pair of hybridized nucleic acid molecules (e.g., polynucleotides) may be complementary along their entire length or, alternatively, along only a part of their sequence. In some cases, all of the nucleotides in a pair of hybridized oligonucleotides are complementary. However, mismatch base pairing between complementary nucleic acids may occur, and such nucleic acids are therefore said to be less than 100% complementary. In particular, the extent of complementarity is usually indicated by the fraction (e.g., the percentage) of mismatched base pairs out of the total number of base pairs in the complementary nucleic acid molecules. There may be at least 60%, 65%, 70%, 75%, 80%, 85%, 90%, 95%, 99%, or greater complementarity between a nucleic acid molecule and its complementary sequence.

The term "quencher," as used herein, generally refers to molecules that may be energy acceptors. Example quenchers, without limitation, include Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare). Examples of fluorophore donor molecules that can be used in conjunction with above quenchers include, without limitation, fluorophores such as Cy3B, Cy3, or Cy5; Dy-Quenchers (Dyomics), such as DYQ-660 and DYQ-661; and ATTO fluorescent quenchers (ATTO-TEC GmbH), such as ATTO 540Q, 580Q, 612Q.

The term "label," as used herein, generally refers to a moiety that is capable of coupling with a species, such as, for example a nucleotide analog. A label may include an affinity moiety. In some cases, a label may be a detectable label that emits a signal (or reduces an already emitted signal) that can be detected, such as a reporter moiety. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after a primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP), tris(hydroxypropyl) phosphine (THP) or enzymatically cleavable (e.g., via an esterase, lipase, peptidase or protease). In some cases, the label may be luminescent; that is, fluorescent or phosphorescent. Labels may be quencher molecules. The term "quencher," as used herein refers to a molecule that can reduce an emitted signal. For example, a template nucleic acid molecule may be configured to emit a detectable signal. Incorporation of a nucleotide or nucleotide analog comprising a quencher can reduce or eliminate the signal, which reduction or elimination is then detected. In some cases, as described elsewhere herein, labelling with a quencher can occur after nucleotide or nucleotide analog incorporation. Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores, Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare); Dy-Quenchers (Dyomics), such as DYQ-660 and DYQ-661; and ATTO fluorescent quenchers (ATTO-TEC GmbH), such as ATTO 540Q, 580Q, 612Q. In some cases, the label may be a type that does not self-quench or exhibit proximity quenching. Non-limiting examples of a label type that does not self-quench or exhibit proximity quenching include Bimane derivatives such as Monobromobimane. The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other.

The term "detector," as used herein, generally refers to a device that is capable of detecting a signal, such as a signal indicative of the presence or absence of an incorporated nucleotide or nucleotide analog. A detector may include optical and/or electronic components that may detect signals. Non-limiting examples of detection methods involving a detector include optical detection, spectroscopic detection, electrostatic detection, and electrochemical detection. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The terms "about" and "approximately" shall generally mean an acceptable degree of error for the quantity measured given the nature or precision of the measurements. Typical, examples of degrees of error are within 20 percent (%), within 10%, or within 5% of a given value or range of values. Alternatively, and particularly in biological systems, the terms "about" and "approximately" may mean values that are within an order of magnitude, within 5-fold, or within 2-fold of a given value. Numerical quantities given herein are approximate unless stated otherwise, meaning that the term "about" or "approximately" can be inferred when not expressly stated.

Methods and Systems for Improved Sequencing

Quantifying long repeating sequences, such as homopolymers or dinucleotide repeating sequences or trinucleotide repeating sequences, can be difficult, for example, because systematic and random errors can compound to produce large errors in length determination. Long repeating regions, such as long homopolymers, can be relatively rare in genomes. The practical challenge of long homopolymer sequencing is to correctly determine such rare events efficiently. The present disclosure provides a solution that can be used in two-dimensional (2D) arrayed colony (either random or patterned) sequencing by synthesis (SBS) or sequencing by ligation (SBL) processes.

The present disclosure provides a method to detect a repeating region (e.g., homopolymer) of a target nucleic acid molecule. The present disclosure also provides a method to accurately determine the length of the repeating region of the target nucleic acid. In some cases, the disclosed method can be used to detect the repeating regions before or after performing SBS, and can improve SBS accuracy. In some cases, the SBS is flow SBS. In some cases, the method can be used to disambiguate specific sequences (e.g. homopolymers, dinucleotide or trinucleotide repeating sequences, GC-rich sequences, etc.) that are difficult to quantify in the sequencing assay. In some cases, the method may comprise hybridizing a targeted probe to the repeating region of the target nucleic acid molecule, thereby detecting the repeating region. The repeating region can have any length. The targeted probe can comprise an observable signal which can be detected. In some embodiments, the targeted probe can comprise a reporter moiety, such as a fluorescent label. The present disclosure also provides a method to verify or re-compute the lengths of repeating regions from the detected signals. In some cases, the method can be used to detect repeating region(s) in a single molecule template. In some cases, the method can be used to detect repeating region(s) in a clonal population of a nucleic acid template.

In an aspect, a method for homopolymer detection comprises subjecting a first nucleic acid sample of a subject to a first assay to generate a first data set. The first data set may comprise a nucleic acid sequence of a target nucleic acid molecule from the first nucleic acid sample. Next, a second nucleic acid sample of the subject may be subjected to a second assay to generate a second data set. The second data set may comprise a homopolymer sequence of the target nucleic acid molecule. The first assay and the second assay may be of different types. A programmed computer may be used to combine the first data set and the second data set to generate a combined data set. The combined data set can comprise the nucleic acid sequence and the homopolymer sequence. In some instances, the homopolymer sequence can be determined at an accuracy of at least about 70%, 75%, 80%, 85%, 90%, 95%, 96%, 97%, 98%, 99%, or higher. Alternatively, the homopolymer sequence can be determined at an accuracy of less than about 70%.

The first assay and second assay may be performed in any order. For example, the first assay may be performed subsequent to the second assay or the second assay may be performed subsequent to the first assay. In some instances, the first assay may be performed in parallel with the second assay simultaneously or substantially simultaneously (e.g., in real-time). One or more other procedures or operations (e.g., one or more assays) may be performed between the first assay and the second assay or between the second assay and the first assay.

A nucleic acid sample may comprise one or more nucleic acid molecules. The first nucleic acid sample and the second nucleic acid sample may comprise the same target nucleic acid molecule. For example, the first nucleic acid sample and the second nucleic acid sample may be or comprise copies (e.g., clonal copies) of the target nucleic acid molecule. The first nucleic acid sample and the second nucleic acid sample can be the same or different, and/or they can both be colonies generated from sample nucleic acid templates. In some instances, the second nucleic acid sample can be derived from the first nucleic acid sample, or vice versa. For example, where the target nucleic acid molecule is a deoxyribonucleic acid (DNA) molecule, the target nucleic acid molecule may be subjected to nucleic acid amplification. Such nucleic acid amplification may be, for example, polymerase chain reaction, emulsion-based amplification, or bridge amplification. Alternatively or in addition to, where the target nucleic acid molecule is a ribonucleic acid (RNA) molecule, the target nucleic acid molecule may be subjected to reverse transcription. For example, where a first copy or derivative and a second copy or derivative is generated from a target nucleic acid molecule, in some instances, the first assay may be performed on the first copy or derivative and the second assay may be performed on the second copy or derivative. In some instances, the first assay may be performed on the target nucleic acid molecule and the second assay may be performed on either the first or second copy or derivative. In some instances, the first assay may be performed on the target nucleic acid molecule at a first time point, and the second assay may be performed sequentially on the same target nucleic acid molecule at a second time point. In such cases, for example, one or more modifications made to the target nucleic acid molecule by the first assay may be reversed before performing the second assay on the target nucleic acid molecule.

The target nucleic acid molecule may be single-stranded or double-stranded. The target nucleic acid molecule may be a polynucleotide. The length of the polynucleotide can vary. For example, the polynucleotide can be at least about 1, 50, 100, 200, 300, 400, 500, 600, 700, 800, 900, 1,000, 2,000, 3,000, 4,000, 5,000, 6,000, 7,000, 8,000, 9,000, 10,000, 50,000, 100,000, or more nucleotides in length. Alternatively or in addition to, the polynucleotide can be at most about 500,000, 400,000, 300,000, 200,000, 100,000, 50,000, 10,000, 9,000, 8,000, 7,000, 6,000, 5,000, 4,000, 3,000, 2,000, 1,000, 900, 800, 700, 600, 500, 400, 300, 200, 100, 50 or fewer nucleotides in length.

The target nucleic acid molecule can comprise one or more specific regions to sequence. Examples of specific regions can include, but are not limited to, GC-rich regions and repeated regions that are relatively difficult to sequence. The repeated regions can be, for example, homopolymer regions (e.g., same type of nucleotide repeating consecutively), dinucleotide repeating regions (e.g., same pair of nucleotides repeating consecutively), trinucleotide repeating regions (e.g., same trio of nucleotides repeating consecutively), and the like. In some cases, the target nucleic acid molecule can comprise one or more repeating regions. For example, the target nucleic acid molecule can comprise at least 2, 3, 4, 5, 6, 7, 8, 9, or more repeating regions. In some cases, multiple homopolymer regions may be consecutive or separated by a non-homopolymer region with one or more nucleotides. A homopolymer region can comprise at least about 2, 3, 4, 5, 6, 7, 8, 9, 10, 20, 30, 40, 50, 60, 70, 80, 90, 100, or more nucleotides of the same type consecutively. Alternatively, a homopolymer region can comprise at most about 100, 90, 80, 70, 60, 50, 40, 30, 20, 10, 9, 8, 7, 6, 5, or fewer nucleotides of the same type consecutively. A repeating region can comprise at least about 2, 3, 4, 5, 6, 7, 8, 9, 10, 20, 30, 40, 50, 60, 70, 80, 90, 100, 200, 300, 400, 500, 1000 or more repeating units (e.g., one nucleotide, pair of nucleotides, trio of nucleotides, etc.) consecutively. Alternatively, a repeating region can comprise at most about 1000, 500, 400, 300, 200, 100, 90, 80, 70, 60, 50, 40, 30, 20, 10, 9, 8, 7, 6, 5, or less repeating units consecutively.

The first assay and/or second assay may be different assays. Alternatively, the first assay and the second assay may be the same type of assay performed under different operating parameters. Alternatively, the first assay and the second assay may be the same type of assay performed under the same operating parameters. The methods described herein can be combined with current sequencing methods to improve the accuracy of sequence determination.

The first nucleic acid sample may be subjected to the first assay to generate the first data set. The first data set may comprise a nucleic acid sequence of the target nucleic acid molecule in the first nucleic acid sample. For example, the first assay may be a first type of sequencing assay.

In some cases, the first assay may employ a short-read sequencing approach, such as sequencing by ligation (SBL) or sequencing by synthesis (SBS). In SBL approaches, a probe sequence that can be bound to a fluorophore can be hybridized to a nucleic acid fragment, and ligated to an adjacent oligonucleotide for imaging. The emission spectrum of the fluorophore can indicate the identity of the base or bases complementary to specific positions within the probe. In SBS approaches, a polymerase may be used and a signal, such as a fluorophore or a change in ionic concentration, can identify the incorporation of a nucleotide into an elongating strand.

In most SBL and SBS approaches, a template of the target nucleic acid molecule may be clonally amplified on a solid surface. Having many thousands of identical copies of a template in a defined area may ensure that the detected signal can be distinguished from background noise. Massive parallelization can be facilitated by the creation of many millions of individual SBL or SBS reaction centers, each with its own clonal template. A sequencing platform can collect information from many millions of reaction centers simultaneously, thus sequencing many millions of nucleic acid molecules in parallel. Such sequencing assay can be referred to as massively parallel sequencing. Some examples of massive parallel sequencing providers include, for example, SOLiD®, Complete Genomics®, Illumina®, Qiagen®, Roche 454®, Ion Torrent®, Pacific Biosciences®, Oxford Nanopore Technologies®, and 10× Genomics®. Examples of SBL platforms include, but are not limited to, SOLID® and Complete Genomics®. SBS approaches can be classified either as cyclic reversible termination (CRT) or as single-nucleotide addition (SNA). Examples of CRT platforms include, but are not limited to, Illumina® and Qiagen®. Examples of SNA platforms include, but are not limited to, 454® and Ion Torrent®.

A template for the target nucleic acid molecule may be prepared from various linear or circular sources of polynucleotides, such as dsDNA, ssDNA, cDNA, RNA and synthesized or naturally occurring oligonucleotides. A template can also be prepared using dsDNA from a biological sample. The genomic DNA may be extracted using an extraction kit commercially available. Then, the dsDNA may be fragmented to any length or a specific length, such as via mechanical (e.g., focused electroacoustic, nebulization, sonication, vortex) or enzymatic (e.g. Fragmentase) fragmentation. In some cases a size (or length) of a fragment is between 100 and 1,000 nucleotides. However, any size of a fragment can be used. For example, the length can be at least about 1, 50, 100, 500, 1,000, 5,000, 10,000, 50,000, 100,000 or more nucleotides in length. Alternatively or in addition to, the length can be at most about 500,000, 100,000, 50,000, 10,000, 5,000, 1,000, 500, 100, 50 or fewer nucleotides in length. In certain instances, the target nucleic acid molecule may be an entire strand of genomic DNA or a portion or fragment thereof.

The template can be amplified to generate a clonal copy, clonal copies, or clonal populations which comprise template-homologous strands (called "template strands" or "reverse strands" herein) and/or template-complementary strands (called "primer strands" or "forward strands" herein). Each clonal copy exhibits homology to the original template molecule. A clonal population can refer to a colony. Within a clonal population, each clonal copy is amplified from the same template molecule. In some cases, clonality can be maintained in the resulting amplified nucleic acid populations by maintaining association between template strands and its primer strands, thereby effectively associating or "tethering" associated clonal progeny together and reducing the probability of cross-contamination between different clonal populations. A clonal population of substantially identical nucleic acids can have a spatially localized or discrete macroscopic appearance. A clonal population can resemble a distinct spot or colony. In some cases, one or more amplified nucleic acids in the clonal population can be attached to a support.

One or more nucleic acid molecules described herein may be immobilized on a support, such as prior to, during, and/or subsequent to amplification or sequencing. The support may be a material having a surface on or to which additional matter can be coupled to or appended (e.g., as described herein). The support may be a solid support, such as a slide, a bead, a resin, a chip, an array, a matrix, a membrane, a nanopore, a substantially planar surface, or a gel. The solid support may, for example, be a flat substrate (such as glass, plastic, silicon, etc.) or a bead (e.g., within a well of a substrate). The substrate may have surface properties, such as textures, patterns, microstructure coatings, surfactants, or any combination thereof to retain the bead at a given location (such as in a position to be in operative communication with a detector). When using a support that is substantially planar, the support may be physically separated into regions, for example, with trenches, grooves, wells, or chemical barriers (e.g., hydrophobic coatings, etc.). The support may be a flow cell or an open substrate. The support may comprise a biological support, a non-biological support, an organic support, an inorganic support, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. Immobilization on the support may be aided by an adaptor. In some instances, a nucleic acid molecule can be attached to a support using one or more phosphoramidite linkers.

There can be several different strategies used to generate clonal template populations: bead-based, solid-state and nucleic acid nanoball generation. The first step of template generation can be fragmentation of the sample nucleic acid, followed by ligation to a common adaptor set for clonal amplification and sequencing. For bead-based preparations, one adaptor is complementary to an oligonucleotide fragment that is immobilized on a bead. Using emulsion PCR (emPCR), the template can be amplified such that as many as one million clonal fragments are immobilized on a single bead. These beads can be distributed onto a glass surface or otherwise arrayed (e.g., on a PicoTiterPlate from Roche Diagnostics®). Solid-state amplification eschews the use of emPCR in favor of amplification directly on a slide. In this approach, forward and reverse primers are covalently bound to the slide surface, either randomly or on a patterned slide. These primers can provide complementary ends to which single-stranded templates can bind. Precise control over template concentration can enable the amplification of templates into localized, non-overlapping clonal clusters, thus maintaining spatial integrity. A clonal population of template nucleic acid can also be generated in solution. In this case, nucleic acid template undergoes an iterative ligation, circularization and cleavage process to create a circular template, with four distinct adaptor regions. Through the process of rolling circle amplification (RCA), up to 20 billion discrete nucleic acid nanoballs are generated. The nanoball mixture is then distributed onto a patterned slide surface containing features that allow a single nanoball to associate with each location.

In emulsion PCR, fragmented DNA templates can be ligated to adapter sequences and can be captured in an aqueous droplet (micelle) along with a bead covered with complementary adapters, deoxynucleotides (dNTPs), primers, and DNA polymerase. PCR can be carried out within the micelle, covering each bead with thousands of clonal copies of the same DNA sequence. In solid-phase bridge amplification, fragmented DNA can be ligated to adapter sequences and bound to a primer immobilized on a solid support, such as a patterned flow cell. The free end can interact with other nearby primers, forming a bridge structure. PCR can be used to create a second strand from the immobilized primers, and unbound DNA can then be removed. In solid-phase template walking, fragmented DNA can be ligated to adapters and bound to a complementary primer attached to a solid support. PCR can be used to generate a second strand. The now double-stranded template can be partially denatured, allowing the free end of the original template to drift and bind to another nearby primer sequence. Reverse primers can be used to initiate strand displacement to generate additional free templates, each of which can bind to a new primer. In DNA nanoball generation, DNA can be fragmented and ligated to the first of four adapter sequences. The template can be amplified, circularized and cleaved with a type II endonuclease. A second set of adapters can then be added, followed by amplification, circularization and cleavage. This process can be repeated for the remaining two adapters. The final product is a circular template with four adapters, each separated by a template sequence. Library molecules undergo a rolling circle amplification step, generating a large mass of concatamers called DNA nanoballs, which can then deposited on a flow cell.

Alternatively or in addition to, the first assay may employ long read sequencing approach, such as single-molecule real-time sequencing approaches or synthetic approaches that rely on existing short read technologies to construct long reads in silico. Examples of single-molecule read-time sequencing platforms include, but are not limited to, Pacific Biosciences® and Oxford Nanopore Technologies®. Examples of synthetic long read platforms include, but are not limited to, Illumina® and 10× Genomics®.

Alternatively or in addition to, the first assay may comprise one or more other sequencing methods or variations to the methods described elsewhere herein. The first nucleic acid sample may be subjected to the first assay to generate the first data set. The first data set may comprise a nucleic acid sequence of the target nucleic acid molecule in the first nucleic acid sample.

The second assay may be a second type of sequencing assay. The second assay may be configured to detect and sequence a specific region of the target nucleic acid molecule. For example, the second assay may be a homopolymer detection assay. The second nucleic acid sample may be subjected to the second assay to generate the second data set. The second data set may comprise a homopolymer sequence of the target nucleic acid molecule in the second nucleic acid sample. Alternatively, the second data set may comprise a different specific sequence (e.g., repeating region sequence) of the target nucleic acid molecule.

The second assay may be configured to sequence a specific region, such as a GC-rich region, a homopolymer region, or other repeating regions (e.g., dinucleotide repeating regions, trinucleotide repeating regions, etc.). The assay may use a targeted probe configured to hybridize to the specific region of the target nucleic acid molecule. For example, the targeted probe can hybridize to a GC-rich region, a homopolymer region, or other repeated region. The targeted probe may be configured to identify a length and/or sequence of the specific region. The targeted probe may be part of an array. Hybridization of the targeted probe may be by array hybridization. Array hybridization may be performed using a nucleic acid (e.g., DNA) array. Such array may be a planar array.

The nucleic acid array may comprise a collection of nucleic acid (e.g., DNA) spots attached to a solid surface (e.g., as described herein). Each DNA spot may include a specific nucleic acid sequence. Such nucleic acid sequences may be probes (or reporters or oligonucleotides). The nucleic acid sequences can have various sequences and lengths. The sequences may be targeted. In some examples, the sequences are homopolymer sequences of various lengths. For example, a first spot can have probe molecules with a homopolymer sequence of a first nucleotide (e.g., A) of a length of 40 nucleotides, a second spot can have probe molecules with a homopolymer sequence of the first nucleotide of a length of 80 nucleotides, a third spot can have probe molecules with a homopolymer sequence of the first nucleotide of a length of 120 nucleotides, and so on.

The probes can be a short section of a gene or other nucleic acid element that is used to hybridize a nucleic acid molecule (e.g., DNA or RNA). Probe-target hybridization may be detected and quantified by detection of signals from the spots, such as optical signals. This may be performed, for example, using fluorophore-, silver-, or chemiluminescence-labeled nucleic acid molecules (probes and/or targets).

For example, the targeted probe may be a homopolymer probe that can hybridize to the homopolymer region of the target nucleic acid molecule, and determine a length and/or sequence of the homopolymer region. The homopolymer probe may comprise a homopolymer region which hybridizes to the homopolymer region of the target nucleic acid molecule. In some cases, the homopolymer probe may further comprise one or more randomer regions, as described elsewhere herein. In some cases, the homopolymer probe may be labeled with one or more dye molecules. In some cases, the homopolymer probe may comprise at least one nucleotide variant, such as nonstandard nucleotide(s), non-natural nucleotide(s), nucleotide analog(s), and/or modified nucleotide(s). In some cases, the homopolymer probe may be a homopolymer bracketing probe comprising a first half bracketing probe and a second half bracketing probe which may be ligated to form a complete homopolymer probe.

The homopolymer probe can be any length of nucleotides. For example, the homopolymer probe may be at least about 1, 2, 3, 4, 5, 6, 7, 8, 9, 10, 12, 15, 20, 25, 30, 40, 50, 100 or more nucleotides in length. Alternatively, the homopolymer probe may be at most about 100, 50, 40, 30, 20, 10, 9, 8, 7, 6, 5, 4, 3, or fewer nucleotides in length. In some instances, the homopolymer region in the homopolymer probe may be at least about 1, 2, 3, 4, 5, 6, 7, 8, 9, 10, 20, 30, 40, 50, 100 or more nucleotides in length. Alternatively, the homopolymer region in the homopolymer probe may be at most about 100, 50, 40, 30, 20, 10, 9, 8, 7, 6, 5, 4, 3, or fewer nucleotides in length. The homopolymer region in the homopolymer probe can be an exact match, or shorter than, or longer than the homopolymer region of the target nucleic acid molecule. The homopolymer probe can be an exact match, or shorter than, or longer than the homopolymer region of the target nucleic acid molecule.

The homopolymer probe or any component of the homopolymer probe (e.g., a nucleobase, sugar moiety, backbone) described herein may be modified in order to achieve, reduce, remove, or otherwise modify particular properties or activities of the homopolymer probe. For example, the homopolymer probe or one or more components of the homopolymer probe may be modified to increase specificity of binding and/or sensitivity to number of matched bases.

In some cases, the homopolymer probe may comprise one or more nucleotide analogs, including derivatives wherein the sugar is modified, such as in 2'-O-methyl, 2'-deoxy-2'-fluoro, and 2',3'-dideoxynucleoside derivatives, nucleic acid analogs based on other sugar backbones, such as threose, locked nucleic acid (LNA) derivatives, bicyclo sugars, or hexose, glycerol and glycol sugars, nucleic acid analogs based on non-ionic backbones, such as "peptide nucleic acids," these nucleic acids and their analogs in non-linear topologies, such as dendrimers, comb-structures, and nano-structures, and/or these nucleic acids and their analogs carrying tags (e.g., fluorescent, functionalized, or binding) bound to their ends, sugars, or nucleobases.

The homopolymer probe may comprise one or more backbone modifications and/or one or more sugar moiety modifications. In some cases, the backbone of the homopolymer probe may be modified by various chemical modifications. Modifications of homopolymer probes include, but are not limited to, 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (LNAs). Further examples of inhibitory nucleic acids include modified oligonucleotides (2'-O-methylated or 2'-O-methoxyethyl), LNA, morpholino oligonucleotides, peptide nucleic acids (PNAs), PNA-peptide conjugates, and LNA/2'-O-methylated oligonucleotide mixmers. In some embodiments, an acrylated methyl oleate (AMO) may comprise a 2'-O-methyl modified ribose sugars with terminal phosphorothioates and a cholesterol group at the 3' end ("antagomir"). Examples of other modifications are detailed in, for example, Valóczi et al., Nucleic Acids Res. 32(22):e175 (2004) Fabiani and Gait, RNA 14:336-46 (2008); Lanford et al., Science 327 (5962):198-201 (2010); Elmen et al., Nature 452:896-9 (2008); Gebert et al., Nucleic Acids Res. 42(1):609-21 (2013); Kloosterman et al., PLoS Biol 5(8):e203 (2007); and Elmen et al., Nucleic Acids Res. 36:1153-1162 (2008).

In some examples, each monomer of the homopolymer probe can be modified in the same way. For example each linkage of the backbone of the homopolymer probe may comprise a phosphorothioate linkage or each ribose sugar moiety may comprise a 2'O-methyl modification. In some examples, there may be a combination of different modifications. For example, a homopolymer probe can comprise a combination of phosphorodiamidate linkages and sugar moieties comprising morpholine rings (morpholinos).

In some cases, a homopolymer probe may comprise a locked nucleic acid (LNA) nucleotide analog. Some embodiments of LNA nucleotide analogs are bicyclic nucleic acid analogs that contain one or more 2'-O, 4'-C methylene linkages, which effectively lock the furanose ring in a C3'-endo conformation. This methylene linkage "bridge" can restrict the flexibility of the ribofuranose ring and lock the structure into a rigid bicyclic formation. Homopolymer probes comprising LNA nucleotide analogs can have a greater affinity and specificity to their target nucleic acid molecule than do natural DNA counterparts. LNAs can hybridize to complementary nucleic acids even under adverse conditions, such as under low salt concentrations. See, e.g., U.S. Pat. Nos. 6,130,038; 6,268,490; and 6,670,461.

In some cases, a homopolymer probe may comprise a peptide nucleic acid (PNA) nucleotide analog. In some cases, the negatively charged sugar-phosphate backbone of DNA can be replaced by a neutral polyamide backbone composed of N-(2-aminoethyl) glycine units. The chemical configuration of PNA typically enables the nucleotide bases to be positioned in approximately the same place as in natural DNA, allowing PNA to hybridize with the complementary DNA or RNA sequence.

The homopolymer probe may comprise one or more randomer regions comprising random sequences. As used herein, the terms "randomer region" and "random sequence region" may be used interchangeably. In some cases, the randomer region may be located at the 5' end of the homopolymer region of the homopolymer probe. In other cases, the randomer region may be located at the 3' end of the homopolymer region of the homopolymer probe. In some other cases, the homopolymer region may be flanked by randomer regions on both sides. The length of the randomer region can vary. For example, the randomer region can be at least about 1, 2, 3, 4, 5, 6, 7, 8, 9, 10, 20, 30, 40, 50, or more nucleotides in length. Alternatively, the randomer region may be at most about 50, 40, 30, 20, 10, 9, 8, 7, 6, 5, 4, 3, or fewer nucleotides in length. The randomer region may contain a sequence of randomized bases. In some cases, each given position (or base) of the random sequence region may contain one base that is selected from all four types of bases (e.g., A, T, C, and G). In other cases, a position (or a base) of the random sequence region may contain one nucleotide selected from only three types of the bases. For example, for the base of the randomer region that is immediately adjacent to the homopolymer region, the base may be selected from one of three types of bases that is not the type of base that is within the homopolymer region. As an example, for a homopolymer probe that contains a homopolymer region of A's, the position immediately adjacent to the homopolymer region, either at the 5' end or 3' end, may be selected from T, C, or G.

In some cases, different batches of targeted probes (e.g., homopolymer probes) may be introduced to a nucleic acid sample. The different batches of probes may have the same total length, but vary in the respective lengths of the homopolymer region and the random sequencing region(s). For example, all targeted probes may have the same length which may be equal to the maximum length that the homopolymer region in the target nucleic acid needs to be reliably differentiated (N_max). The sequencing system may reliably read a minimum length of the homopolymer region (N_min). The introduced targeted probes can have a homopolymer region comprising a length: N_min, N_min+1, N_min+2, N_min+3 . . . N_max. In these cases, the remaining bases of the targeted probes can be random sequences to make the total length of the homopolymer probe N_max. Different batches of targeted probes can be introduced in sequential flow runs.

In certain examples, the homopolymer probe may be a homopolymer bracketing probe comprising a first half of a bracketing probe and a second half of a bracketing probe, wherein the first half of the bracketing probe binds to a first segment of the homopolymer region of the template, and the second half of the bracketing probe binds to a second segment of the homopolymer region of the template. In some cases, the first half of bracketing probe and the second half of bracketing probe may be ligated to form a complete homopolymer probe. In some cases, there may be a gap region between the first half of the bracketing probe and the second half of the bracketing probe after hybridizing to the homopolymer region of the template. The gap region can be at least about 1, 2, 3, 4, 5, 6, 7, 8, 9, 10, or more nucleotides in length. Alternatively, the gap region may be at most about 10, 9, 8, 7, 6, 5, 4, 3, or fewer nucleotides in length. In these cases, a non-strand displacing extension can be performed to fill in the gap region followed by a ligation step to form a complete homopolymer probe. In some cases, the non-strand displacing extension can be performed with labeled nucleotides or nucleotide analogs so that labels can be incorporated into the homopolymer probe. A bracketing probe can further comprise a randomer region, as described elsewhere herein. A bracketing probe can be labeled with one or more reporter moieties, as described elsewhere herein. In certain cases, homopolymer bracketing probes can be labeled with a FRET dye pair, wherein the first half of bracketing probe can be labeled with a FRET donor and the second half of bracketing probe can be labeled with a FRET acceptor. Example 9 and FIG. 8, described elsewhere herein, illustrate an example of a pair of homopolymer bracketing probes with a FRET dye pair.

In some cases, the homopolymer probe may be labeled with one or more reporter moieties, such as fluorophores or dye molecules. In some cases, the homopolymer probe can be labeled with different numbers of reporter moieties to indicate a different length of the homopolymer probe having the same sequence. In some cases, the homopolymer probe can be labeled with different numbers of reporter moieties to indicate a different length of the homopolymer region of the homopolymer probe. In some other cases, different reporter moieties can be used to label different homopolymer probes having different sequences or different length. For example, different reporter moieties can be different dye molecules. In some cases, the homopolymer probes can be labeled with the same dye molecules having different intensities in different configurations. Alternatively, the homopolymer probe may not be labeled with a reporter moiety. In some cases, the homopolymer probes can be a mixed population of labeled and un-labeled probes, and the different type/length may be differentiated by the proportion of labeled probes.

The homopolymer probe may emit an observable signal. For example, in some cases, the homopolymer probe may not be labeled and the observable signal may be electron signal or electromagnetic signal. For example, semiconductors can be used to detect electron signals, and nuclear magnetic resonance (NMR) can be used to detect electromagnetic signals. In other cases, the homopolymer probe is labeled with one or more reporter moieties, as described elsewhere herein, and the observable signal may be an optical signal. Detection of the one or more reporter moieties may involve imaging by a detector (e.g., optical detector).

An observable signal may be any signal that can be detected. For example, the signal can be an electronic signal, fluorescence signal, or electromagnetic signal. In some cases, such a signal may be indicative of incorporation of one or more nucleotides or nucleotide analogs. In some cases, such a signal may be directly from the incorporated nucleotides or nucleotide analogs, for example, a hydrogen ion released from the incorporated nucleotides or nucleotide analogs. In some cases, a reporter moiety that is coupled to a nucleotide or nucleotide analog can generate such a signal, which nucleotide or nucleotide analog may be used in a primer extension reaction. Coupling may be covalent or non-covalent (e.g., via ionic interactions, Van der Waals forces, etc.). Where covalent coupling is implemented, the reporter moiety may be coupled to the nucleotide or nucleotide analog via a linker, with non-limiting examples that include aminopropargyl, aminoethoxypropargyl, polyethylene glycol, polypeptides, fatty acid chains, hydrocarbon chains and disulfide linkages. In some cases, the linker is cleavable, such as photocleavable (e.g., cleavable under ultra-violet light), chemically-cleavable (e.g., via a reducing agent, such as dithiothreitol (DTT), tris(2-carboxyethyl) phosphine (TCEP)) or enzymatically cleavable (e.g., via an esterase, lipase, peptidase or protease). In some cases, the linker may be non-cleavable. In some examples, the reporter moieties comprise molecular structures that, once attached to a nucleic acid sequence, provide a distinct characteristic that is not inherent to those nucleic acid molecules. In some cases the reporter moieties may create unique optical characteristics. In some cases, the reporter moieties can be used as a single signal generating entity or may be one of a pair of reporter moieties such that one reporter moiety performs the role of an energy donor, and the other reporter moiety performs the role of an energy acceptor. Energy donors and/or energy acceptors can both be fluorophore molecules. Whether a fluorophore is a donor or an acceptor may be based on its excitation and emission spectra, and the fluorophore with which it is paired.

A reporter moiety can be detectable by the presence of or a change in, color, fluorescence, reflectance, chemiluminescence, light polarization, light scattering, precipitation, x-ray scattering, electron spin resonance, or the deposition of an electron-rich substrate for visualization by electron microscopy. A reporter moiety may be detectable by its optical properties. The detectable response may be the presence of or a change in fluorescence, such as intensity, excitation or emission wavelength distribution of fluorescence, fluorescence lifetime, fluorescence polarization, or a combination thereof. Where the reporter moiety is a fluorophore, the reporter moiety may be a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a porphyrin, a salicylate, an anthranilate, an azulene, a perylene, a pyridine, a quinoline, a coumarin (including hydroxycoumarins and aminocoumarins and fluorinated and sulfonated derivatives thereof), a 4-bora-3a,4a-diaza-s-indacene (e.g., U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); and U.S. Pat. No. 5,433,896 to Kang, et al. (1995), each of which is entirely incorporated herein by reference), a xanthene, an oxazine or a benzoxazine, a carbazine (U.S. Pat. No. 4,810,636 to Corey (1989), which is entirely incorporated herein by reference), or a phenalenone or benzphenalenone (U.S. Pat. No. 4,812,409 Babb et al. (1989), which is entirely incorporated herein by reference), or a lanthanide chelate. In some embodiments, where the reporter moiety is a fluorophore, the reporter moiety is a carbazine, an oxazine, a coumarin, a xanthene, a naphthalene, a phenalenone, or a 4-bora-3a,4a-diaza-s-indacene. Where the reporter moiety is a xanthene, the reporter moiety may optionally be a fluorescein, a rhodol (U.S. Pat. No. 5,227,487 to Haugland, et al. (1993), which is entirely incorporated herein by reference), or a rhodamine. As used herein, fluorescein includes benzo- or dibenzofluoresceins, seminaphthofluoresceins, naphthofluoresceins or seminaphthorhodafluors (U.S. Pat. No. 4,945,171 to Haugland, et al. (1990), incorporated by reference). As used herein, oxazines include resorufins, aminooxazineones and diaminooxazines. Other examples of fluorophores include: fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7.

Examples of energy donor/energy acceptor fluorophore pairs include, but are not limited to, cyan fluorescent protein (CFP) and yellow fluorescent protein (YFP); Cy3 and Cy5; fluorescein and tetramethylrhodamine; IAEDANS and fluorescein; EDANS and dabcyl; fluorescein and QSY 7 or QSY 9 dyes; Alex Fluor 350 and Alexa Fluor 488; Alexa Fluor 488 and Alexa Fluor 546, 555, 568, 594, or 647; Alexa Fluor 568 and Alexa Fluor 647; and Alexa Fluor 594 and Alexa Fluor 85.

In some instances, the observable signal may be a product of quenching. In some instances, reporter moieties may be nucleic acid intercalator dyes. Examples include, but are not limited to ethidium bromide, YOYO-1-SYBR Green, and EvaGreen. The nearfield interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Forster resonance energy transfer (FRET) (i.e., energy transfer from the donor to an acceptor that results in radiative energy decay). Other examples of reporter moieties include electrochemical labels, electrostatic labels, colorimetric labels and mass tags. Such labels may be used with the systems and methods disclosed herein.

A detector may be used to detect an observable signal (e.g., as described herein). The detector may be a device that is capable of detecting a signal, including a signal indicative of the presence or absence of an incorporated nucleotide or nucleotide analog. In some cases, the detector can include optical and/or electronic components that can detect signals. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

In some cases, after introducing the homopolymer probe (or batch of homopolymer probes) to the nucleic acid sample, the nucleic acid sample may be imaged at increasing temperatures or increasing concentrations of a denaturing agent, measuring the signal intensity from the one or more reporter moieties, and inferring the number of matching bases between labeled fragments and the template from their annealing or denaturation conditions. In some cases, the hybridization of the homopolymer probe and the target nucleic acid molecule can be performed at a temperature that is lower than the melting temperature ($T_m$) of the duplex formed by the homopolymer probe and the target nucleic acid molecule, and the subsequent imaging operation can be performed at increasing temperatures. The temperature may be increased at increments of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 or more degrees Celsius (° C.). Alternatively, the temperature may be increased at increments of at most about 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less ° C. One or more images can be taken at each temperature increment. The temperature of the hybridization operation can be lower than the $T_m$ of the duplex formed by the homopolymer probe and the target nucleic acid molecule. For example, the temperature of the hybridization operation can be at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 15.0 or more ° C. lower than the $T_m$. Alternatively, the temperature of the hybridization operation can be at most about 15.0, 10.0, 9.0, 8.0, 7.0, 6.0, 5.0, 4.0, 3.0, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less ° C. lower than the $T_m$.

As used herein, the "melting temperature" or "$T_m$" of a nucleic acid molecule generally refers to the temperature at which a polynucleotide dissociates from its complementary sequence. Generally, the $T_m$, may be defined as the temperature at which one-half of the Watson-Crick base pairs in duplex nucleic acid molecules are broken or dissociated (i.e., are "melted") while the other half of the Watson-Crick base pairs remain intact in a double stranded conformation. Where duplex nucleic acid molecules are oligonucleotides that dissociate in a two-state fashion, the $T_m$ of a nucleic acid may also be defined as the temperature at which one-half of the nucleic acid molecules in a sample are in a single-stranded conformation while the other half of the nucleic acid molecules in that sample are in a double-stranded conformation. $T_m$ therefore defines a midpoint in the transition from double-stranded to single-stranded nucleic acid molecules (or, conversely, in the transition from single-stranded to double-stranded nucleic acid molecules). The transition from double-stranded to single-stranded nucleic acid molecules does not occur at a single temperature but, rather, over a range of temperatures. Nevertheless, the $T_m$ may provide a convenient measurement for approximating whether nucleic acid molecules in a sample exist in a single-stranded or double-stranded conformation. As such, the melting temperature of a nucleic acid sample may be readily obtained by simply evaluating a melting profile for that sample (e.g., using a melt curve).

The measurement of $T_m$ can be performed at the same buffer conditions (including the same salt concentration and detergent concentration) as the hybridization conditions. In some cases, the imaging operations at the increasing temperature increments may also be performed at the same buffer conditions as the hybridization step. Various methods for $T_m$ prediction and measurement may be used. For example, theoretical or empirical models that relate duplex stability to nucleotide sequence may be used to predict or estimate melting temperatures for particular nucleic acids. For example, Breslauer et al. (Proc. Natl. Acad. Sci: U.S.A. 1986, 83:3746-3750), which is entirely incorporated herein by reference, describes a model for predicting melting temperatures, known as the "nearest neighbor model". See also, SantaLucia et al., Biochemistry 1996, 35:3555-3562; and SantaLucia, Proc. Natl. Acad. Sci. U.S.A. 1998, 95:1460-1465. Such models are usually calibrated or optimized for particular salt conditions, typically 1 molar (M) Na.

The term "salt concentration" is interchangeably used with the term "ion concentration" and refers, specifically, to the concentration of cations (i.e., positively charged ions within a sample). Types of ions include, but are not limited to, lithium, potassium, sodium, rubidium, cesium and francium. Ions may carry a single or multiple charges. In some cases, monovalent ions are used in the assay. In some cases, the ion concentration may be at least about 1, 2, 3, 4, 5, 6, 7, 8, 9, 10, 20, 30, 40, 50, 60, 70, 80, 90, 100 or more milimolar (mM). Alternatively, the ion concentration may be at most about 100, 90, 80, 70, 60, 50, 40, 30, 20, 10, 9, 8, 7, 6, 5, 4, 3, 2, 1 or less mM.

In some cases, the method may comprise imaging the nucleic acid sample at different denaturing conditions in order to separate duplexes between the homopolymer probe and the target nucleic acid molecule. In some cases, the imaging step may be performed at increasing concentrations of a denaturing agent. This strand separation operation, termed "denaturation," may require aggressive conditions to disrupt the hydrogen and hydrophobic bonds in the double helix. Traditional hybridization experiments, such as in situ hybridization (ISH) assays, may use a formamide-containing solution to denature doubled stranded nucleic acid. Formamide disrupts base pairing by displacing loosely and uniformly bound hydrate molecules, and by causing "formamidation" of the Watson-Crick binding sites. Thus, formamide has a destabilizing effect on double stranded nucleic acids and analogs.

Denaturation may refer to a process in which nucleic acids reduce or lose their tertiary and/or secondary structures by application of compound(s), such as, e.g., a strong acid or base, a concentrated inorganic salt, an organic solvent, and/or by external stress such as e.g. heat. This means that, when denaturation relates to nucleic acids, and when said nucleic acid is double stranded, the strands may separate partially or completely. A denaturing agent may be a substance that is capable of lowering the mutual binding affinity of complementary stands of nucleic acids compared to water. Non-limiting examples of typical denaturing agents include organic solvents such as formamide, urea, DMSO, and tetraalkylammonium halides or combinations thereof. Denaturation conditions can be sequence dependent and can be different under different environmental parameters. The melting temperature ($T_m$) can be used to adjust denaturation conditions to decrease complementary base pairing in the presence of a denaturing agent.

In some cases, the denaturing condition can comprise at least about 0%, 1%, 2%, 3%, 4%, 5%, 10%, 15%, 20%, 25%, 30%, 35%, 40%, 45%, 50%, 60%, 70% or more volume/volume (v/v) denaturing agent (e.g., formamide or dimethyl sulfoxide (DMSO)) in the compositions used in the present disclosure. Alternatively, the denaturing condition can comprise at most about 70%, 60%, 50%, 45%, 40%, 35%, 30%, 25%, 20%, 15%, 10%, 5%, 4%, 3%, 2%, 1% or less v/v denaturing agent in the composition.

Compositions for denaturing nucleic acid duplexes can comprise, for example, buffering agents, accelerating agents, chelating agents, salts, detergents, and blocking agents. For example, the buffering agents may include SSC, HEPES, SSPE, PIPES, TMAC, TRIS, SET, citric acid, a phosphate buffer, such as, e.g., potassium phosphate or sodium pyrophosphate, etc. The buffering agents may be present at concentrations from at least about 0.01×, 0.1×, 1×, 2×, 3×, 4×, 5×, 10×, 15×, 20×, 25×, 30×, 35×, 40×, 45×, 50× or more. Alternatively, the buffering agents may be present at concentration of at most about 50×, 45×, 40×, 35×, 30×, 25×, 20×, 15×, 10×, 5×, 4×, 3×, 2×, 1×, 0.1×, 0.01×, or less.

The accelerating agents may include polymers such as FICOLL, PVP, heparin, dextran sulfate, proteins such as BSA, glycols such as ethylene glycol, glycerol, 1,3 propanediol, propylene glycol, or diethylene glycol, combinations thereof such as Dernhardt's solution and BLOTTO, and organic solvents such as formamide, dimethylformamide, DMSO, etc. The accelerating agent may be present at concentrations from at least about 0.1%, 1%, 2%, 3%, 4%, 5%, 10%, 15%, 20%, 25%, 30%, 35%, 40%, 45%, 50%, 60%, 70%, 80% or higher. Alternatively, the accelerating agent may be present at concentrations from at most about 80%, 70%, 60%, 50%, 45%, 40%, 35%, 30%, 25%, 20%, 15%, 10%, 5%, 4%, 3%, 2%, 1%, 0.1%, or less. Alternatively the accelerating agent may be present at a range of from about 0.1× to about 10×. In an example, formamide may be present at concentrations from about 25% to about 75%, such as 25%, 30%, 40%, 50%, 60%, 70%, or 75%, while DMSO, dextran sulfate, and glycol are present at concentrations from about 5% to about 10%, such as 5%, 6%, 7%, 8%, 9%, or 10%.

The chelating agents may include EDTA, EGTA, etc. The chelating agents may be present at concentrations of at least about 0.1, 0.2, 0.3, 0.4, 0.5, 0.6, 0.7, 0.8, 0.9, 1, 2, 3, 4, 5, 6, 7, 8, 9, 10 mM or more. Alternatively, the chelating agents may be present at concentration of at most about 10, 9, 8, 7, 6, 5, 4, 3, 2, 1, 0.9, 0.8, 0.7, 0.6, 0.5, 0.4, 0.3, 0.2, 0.1 mM or less. In an example, the chelating agents may be present at concentrations from about 0.5 mM to about 5 mM.

The salts may include sodium chloride, sodium phosphate, magnesium phosphate, etc. The salts may be present at concentrations of at least about 1, 2, 3, 4, 5, 10, 20, 30, 40, 50, 100, 200, 300, 400, 500, 600, 700, 800 or more mM. Alternatively, the salts may be present at concentrations of at most about 800, 700, 600, 500, 400, 300, 200, 100, 50, 40, 30, 20, 10, 5, 4, 3, 2, 1 or less mM. In an example, the salts may be present at concentrations from about 10 mM to about 500 mM.

The detergents may include Tween, SDS, Triton, CHAPS, deoxycholic acid, etc. The detergent may be present at concentrations of at least about 0.001%, 0.01%, 0.1%, 1%, 2%, 3%, 4%, 5%, 6%, 7%, 8%, 9%, 10% or higher. Alternatively, the detergent may be present concentration of at most about 10%, 9%, 8%, 7%, 6%, 5%, 4%, 3%, 2%, 1%, 0.1%, 0.01%, 0.001% or less. In an example, the detergents may be present at concentrations from about 0.01% to about 1%.

The compositions used in the present disclosure may include an aqueous composition comprising at least one polar aprotic solvent in an amount effective to denature double-stranded nucleotide sequences. Effective amounts of polar aprotic solvents may include, for example, at least about 1%, 2%, 3%, 4%, 5%, 6%, 7%, 8%, 9%, 10%, 20%, 30%, 40%, 50%, 60%, 70%, 80%, 90%, 95% (v/v) or higher. Alternatively, the effective amounts of polar aprotic solvents may include at most about 95%, 90%, 80%, 70%, 60%, 50%, 40%, 30%, 20%, 10%, 9%, 8%, 7%, 6%, 5%, 4%, 3%, 2%, 1% (v/v) or less. Aqueous compositions comprising a polar aprotic solvent may have reduced toxicity. For example, a less-toxic composition than traditional solutions used in hybridization applications may comprise a composition with the proviso that the composition does not contain formamide, or with the proviso that the composition contains less than 25%, or less than 10%, or less than 5%, or less than 2%, or less than 1%, or less than 0.5%, or less than 0.1%, or less than 0.05%, or less than 0.01% formamide. A less-toxic composition may, in one embodiment, also comprise a composition with the proviso that the composition does not contain dimethyl sulfoxide (DMSO), or with the proviso that the composition contains less than 25%, 10%, 5%, 2%, or less than 1%, or less than 0.5%, or less than 0.1%, or less than 0.05%, or less than 0.01% DMSO.

In some cases, the method may be performed for one or more rounds (e.g. flow runs) with one or more batches of homopolymer probes. In some cases, the one or more batches of homopolymer probes can have different lengths. In some cases, the one or more batches of homopolymer probes can be introduced in a way that the homopolymer probes of each subsequent round are longer than the homopolymer probes of each previous round. In some cases, the homopolymer probes introduced in different batches may have the same total length, but have different lengths in the homopolymer regions of the homopolymer probes. For example, a subsequent batch of homopolymer probes can have a length in the homopolymer region that is at least about 1, 2, 3, 4, 5, 6, 7, 8, 9, 10, 20, 30, 40, 50 or more nucleotides longer than the length of the homopolymer region of the previous batch of probes. Alternatively, the subsequent bath of homopolymer probes can have a length in the homopolymer region that is at most about 50, 40, 30, 20, 10, 9, 8, 7, 6, 5, 4, 3, 2, or 1 nucleotide longer than the length of the homopolymer region of the previous batch of probes. In some cases, the one or more batches of homopolymer probes can have different sequences. In some cases, the one or more batches of homopolymer probes can comprise homopolymer regions with different species, for example, different types of bases. In some cases, the one or more batches of homopolymer probes can comprise a different numbers of reporter moieties. In some cases, the one or more batches of homopolymer probes can comprise different types of reporter moieties, for example, different dye molecules. In some cases, the one or more batches of homopolymer probes can comprise same dye molecules but with different intensities in different configurations.

In some instances, the second assay may be performed after the first assay. For example, a synthesized strand can be generated during SBS. In these cases, the method may further comprise striping away (e.g., denaturing the template duplexes) the synthesized strands following the SBS.

The second nucleic acid sample may be subjected to the second assay, such as the homopolymer detection assay described herein, to generate the second data set. The second data set may comprise a nucleic acid sequence of one or more specific regions of the target nucleic acid molecule, such as a homopolymer region.

The second assay may be performed using homopolymer probes as an example. However, other probes, such as other targeted probes, may be used. For example, the targeted probe may hybridize to non-homopolymer repeating regions, such as dinucleotide repeating regions or trinucleotide repeating regions. The targeted probe may hybridize to non-repeating regions, such as GC regions or any other specified region in the target nucleic acid molecule. Alternatively or in addition to, the second assay may comprise any of the sequencing methods (e.g., SBS, SBL, massively parallel sequencing, etc.) described herein. In some instances, the second assay may be the same type of assay as the first assay. Alternatively, the second assay may be a different type of assay than the first assay. The second assay may comprise any other sequencing methods. The first assay may be performed before the second assay, or vice versa. Alternatively, the first assay and the second assay may be performed substantially simultaneously. The first assay and second assay may be the combination of any two assays yielding sequence data.

For example, the first assay can be a sequencing assay as described herein. In some embodiments, the first assay is a sequencing-by-synthesis assay. In some embodiments, the first assay is a massively parallel sequencing assay. The massively parallel sequencing assay can be performed on any massively parallel sequencer disclosed herein. In some embodiments, the first assay is used to generate a first data set, wherein the first data set comprises a nucleic acid sequence of the target nucleic acid molecule. In some embodiments, the second assay is also a sequencing assay. In some embodiments, the second assay is a homopolymer detection assay. In some embodiments, the second assay comprises array hybridization. In some embodiments, the second assay is used to generate a second data set, wherein the second data set comprises a homopolymer sequence of the target nucleic acid molecule.

A programmed computer may be used to combine the first data set (comprising sequence data of the target nucleic acid molecule) and the second data set (comprising sequence data of a specific region of the target nucleic acid molecule) to generate a combined data set. Computer systems programmed to implement the present disclosure are described with respect to FIG. 9. The combined data set may comprise the nucleic acid sequence and the homopolymer sequence. For example, one or more regions in the sequence data of the first data set may be identified as the one or more specific regions (e.g., homopolymer regions, repeating regions, etc.) sequenced by the second assay, the sequencing data for which is contained in the second data set. Sequencing data of the second data set may comprise a sequence and/or length of the specific region. Sequencing data for the one or more regions in the first data set may be supplemented by data from the second data set. For example, such supplementing may be a replacement, supplementation, re-computation, or verification of the sequencing data in the first data set. In some instances, the homopolymer sequence or other repeating sequence can be determined at an accuracy of at least about 70%, 75%, 80%, 85%, 90%, 95%, 96%, 97%, 98%, 99%, or higher. Alternatively, the homopolymer sequence or other repeating sequence can be determined at an accuracy of less than about 70%.

In some cases, the method may comprise verifying or re-computing the respective length(s) of repeating regions derived from flow SBS using the homopolymer assay signals to confirm or refine length assessments. The disclosed method can be used together with the sequence by sequencing assay to increase the accuracy of homopolymer region determination. In some instances, the homopolymer sequence or other repeating sequence can be determined at an accuracy of at least about 70%, 75%, 80%, 85%, 90%, 95%, 96%, 97%, 98%, 99%, or higher. Alternatively, the homopolymer sequence or other repeating sequence can be determined at an accuracy of less than about 70%.

Systems and methods of the present disclosure may be used to generate a combined data set from any number of data sets. For example, a combined data set may be generated from at least 2, 3, 4, 5, 6, 7, 8, 9, 10, 20, 30, 40, 50 or more data sets. Each of the data sets may be generated from an assay. In some examples, the combined data set is generated from two data sets. Alternatively or in addition to, a combined data set may be generated from at most about 50, 40, 30, 20, 10, 9, 8, 7, 6, 5, 4, 3, 2, or 1 data set. For example, a first data set from a first assay may be combined with a second data set from a second assay, a third data set from a third assay, and a fourth data set from a fourth assay. In this example, the first data set may comprise sequencing data for a target nucleic acid molecule that has a first region that is a G homopolymer region, a second region that is a T homopolymer region, and a third region that is a trinucleotide repeating region. The second data set may comprise sequencing data about the sequence and/or length of the G homopolymer region, the third data set may comprise sequencing data about the sequence and/or length of the T homopolymer region, and the fourth data set may comprise sequencing data about the sequence and/or length of the trinucleotide repeating region. The second, third, and fourth data sets may be combined with the first data set to supplement the sequencing data in the first data set with data about the first, second, and third region from the second, third, and fourth data sets, respectively. For example, such supplementing may be a replacement, supplementation, re-computation, or verification of the sequencing data in the first data set. In some instances, a fraction of a data set (e.g., 0.1, 0.2, 0.3, 0.4, 0.5, 0.6, 0.7, 0.8, 0.9, etc.) may be combined with other data set(s) to generate a combined data set. For example, the fraction of a data set may be an incomplete data set or intermediate data set obtained from an assay. In some instances, a data set that is combined with another data set may be itself a combined data set. For example, a first data set and a first combined data set may be combined to generate a second combined data set. In another example, a first combined data set and a second combined data set may be combined to generate a third combined data set. In some instances, the data sets that are combined to generate the combined data set may or may not come from different assays. For example, a first fraction of a data set obtained from a first assay may be combined with a second fraction of the data set obtained from the first assay to generate the combined data set.

A combined data set may be generated from any number of assays. The assays may be of the same type (e.g., massive parallel sequencing). Alternatively, the assays may be of different types (e.g., massive parallel sequencing and array hybridization). At least some of the data sets may be from the same assay. For example, a combined data set may be generated from at least 2, 3, 4, 5, 6, 7, 8, 9, 10, 20, 30, 40, 50 or more assays. Alternatively or in addition to, the combined data set may be generated from at most 50, 40, 30, 20, 10, 9, 8, 7, 6, 5, 4, 3, 2, 1 assay. In an example, a first data set from a first assay, a second data set from the first assay, a third data set from a second assay, and a fourth data set from a third assay are combined to generated a combined data set.

In another aspect of the present disclosure, a method for determining a sequence of a target nucleic acid molecule comprises subjecting the target nucleic acid molecule to sequencing-by-synthesis to yield sequence data comprising a first sequence of the target nucleic acid molecule. The sequencing-by-synthesis may generate a nucleic acid molecule that is complementary to the target nucleic acid molecule, as described elsewhere herein. Next, the nucleic acid molecule may be removed from the target nucleic acid molecule. Separately, a homopolymer probe may be hybridized to a homopolymer region of the target nucleic acid molecule, as described elsewhere herein. For example, such hybridization may occur prior to, subsequent to, and/or in parallel with the SBS. The homopolymer probe may yield an observable signal that is indicative of a presence of the homopolymer region. Next, the observable signal may be detected to identify a homopolymer sequence of the homopolymer region. The sequence data from the sequencing-by-synthesis assay (comprising the first sequence of the target nucleic acid molecule) may be combined with the homopolymer sequence identified from the observable signal to generate a second sequence of the target nucleic acid molecule. The second sequence may comprise the first sequence and the homopolymer sequence.

In another aspect of the present disclosure, a method for determining a sequence of a nucleic acid sample comprises using a massively parallel sequencer to identify a first nucleic acid sequence of the nucleic acid sample. Separately, a targeted probe may be used to identify a second nucleic acid sequence of the nucleic acid sample, as described elsewhere herein. In some embodiments, the targeted probe may be targeted to an array and the hybridization may be array hybridization. The assay using the massively parallel sequencer and the assay using the targeted probe may be performed independent of each other. A programmed computer may generate a consensus sequence from the first nucleic acid sequence and the second nucleic acid sequence. The consensus sequence may have an accuracy of at least about 70%, 75%, 80%, 85%, 90%, 95%, 96%, 97%, 98%, 99%, or higher. Alternatively, the consensus sequence can have an accuracy of less than about 70%.

In yet another aspect of the present disclosure, a method for determining a first length of a homopolymer region of a target nucleic acid molecule comprises generating a clonal copy of the target nucleic acid molecule. The clonal copy may comprise a copy of the homopolymer region. Next, a homopolymer probe having a second length may be hybridized to the copy of the homopolymer region. The first length and the second length may be the same. The first length and the second length may be different, such that the homopolymer probe has a different length than the homopolymer region of the target nucleic acid molecule, as described elsewhere herein. The sequence of the copy of the homopolymer region may be complementary to the sequence of the homopolymer probe. The homopolymer probe may comprise an observable signal. The observable signal may be detected to determine the first length. In some instances, the homopolymer detection may be followed by, or performed prior to, or in parallel with, a sequencing assay, such as a SBS assay as describe elsewhere herein. For example, the method may further comprise stripping off the synthesized strand before performing the homopolymer detection.

The different assays may be performed on a surface, such as, for example, a flow cell. A first assay and a second assay may be performed in the same flow cell. Alternatively, the first assay and the second assay may be performed in different flow cells. The reagents and probes used in the current methods can be flowed into the flow cell in different rounds (or flow runs). Different homopolymer probes can be flowed into the flow cell in different rounds (or flow runs).

The reagents and/or probes used herein can be provided in a kit. In some embodiments, the kit can contain reagents for sequencing. In some embodiments, the kit can contain targeted probes useful for sequence detection. In some embodiments, the kit can contain reagents for homopolymer detection. In some embodiments, the kit can contain homopolymer probes useful for homopolymer detection. In some embodiments, the kit can contain one or more software modules programmed to combine or otherwise consolidate one or more data sets, as described elsewhere herein.

Computer Systems

Figure 9:
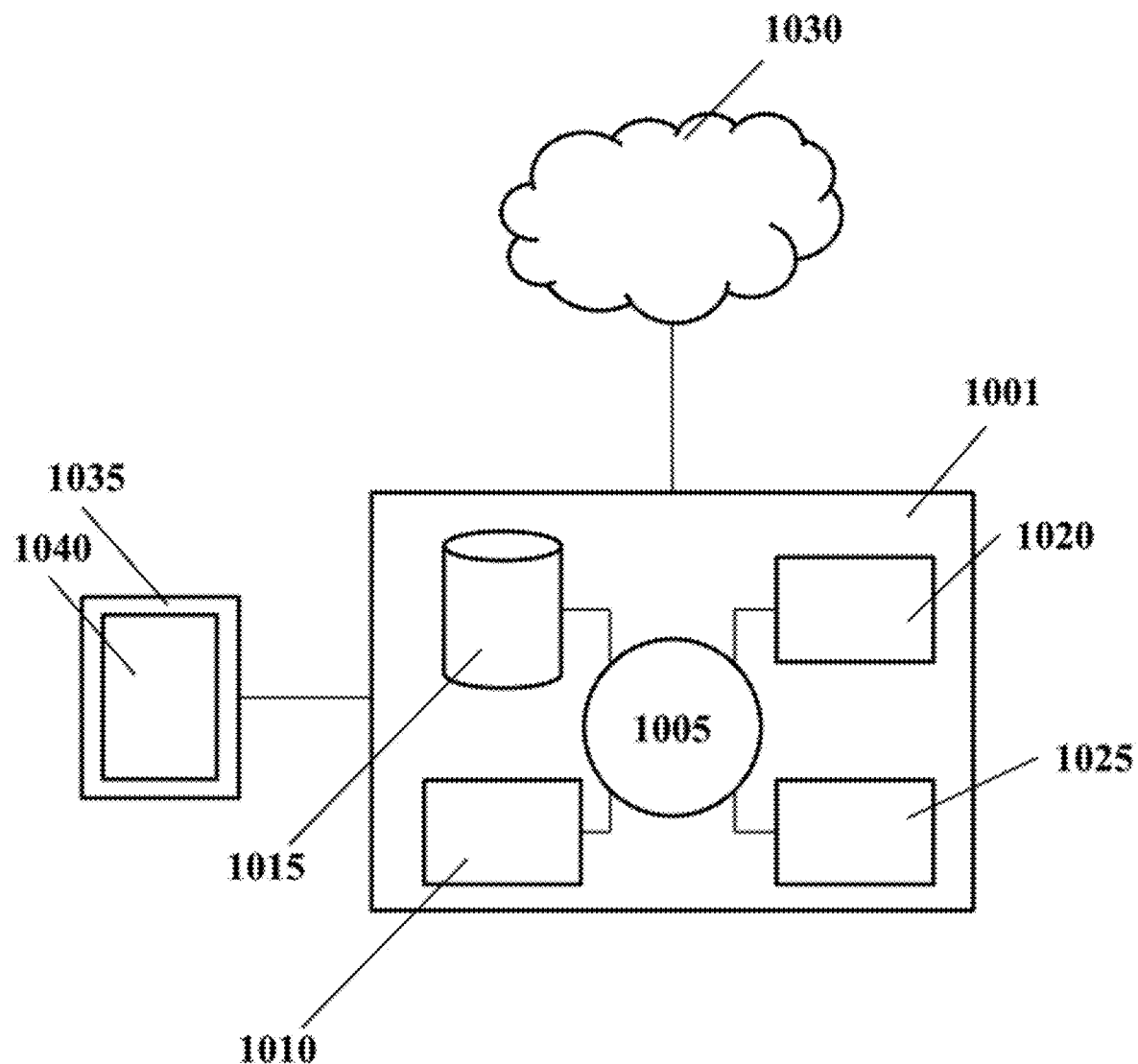
FIG. 9 shows a computer system that is programmed or otherwise configured to implement methods provided herein.

The present disclosure provides computer systems that are programmed to implement methods of the disclosure. FIG. 9 shows a computer system 1001 that is programmed or otherwise configured to perform nucleic acid sequencing and/or homopolymer detection. The computer system 1001 can combine two or more data sets to yield a combined or consensus data set, for example for sequencing data sets. The computer system 1001 can regulate various aspects of the present disclosure, such as, for example, performing nucleic acid sequencing, sequence analysis, homopolymer detection and analysis, and temperature control. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, results of nucleic acid sequence and homopolymer detection (e.g., sequence reads, consensus sequences, homopolymer reads, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, implement methods and systems of the present disclosure, such as combined two or more data sets to yield a combine data set with higher accuracy sequencing data.

Kits

The present disclosure provides kits for use with methods and systems described herein. A kit can include one or more nucleic acid probes. The one or more nucleic acid probes may be one or more targeted probes described elsewhere herein. For example, each probe may be labeled with one or more reporter moieties. The kit can also include one or more nucleotides or nucleotide analogs described herein. The kit can include reagents and buffers necessary for performing the methods described herein. For example, the kit can include reagents for performing one or more sequencing assays described herein (e.g., first assay, second assay). In some embodiments, the kit can contain reagents for homopolymer detection or repeated region detection. In some embodiments, the kit can contain homopolymer probes useful for homopolymer detection. In some embodiments, the kit can contain other targeted probes configured to hybridize and detect other regions that may or may not be a repeating region. In some embodiments, the kit can contain one or more software modules programmed to combine or otherwise consolidate one or more data sets, as described elsewhere herein. The software module may, for example, be programmed to identify a location of a repeating region in the target nucleic acid molecule. The software module may, for example, be programmed to determine a length of a repeating region in the target nucleic acid molecule. The software module may, for example, be programmed to determine a sequence of the target nucleic acid molecule with at least 70%, 75%, 80%, 85%, 90%, 95%, 99% or more accuracy. Alternatively, the software module may be programmed to determine the sequence of the target nucleic acid molecule with less than 70% accuracy. A kit may include any combination of the above. A kit may include all of the above.

The kit can include a carrier, package, or container that may be compartmentalized to receive one or more containers, such as vials, tubes, and the like, each of the container(s) comprising one of the separate elements, such as the nucleic acid probes and buffers, to be used in a method described herein. Suitable containers include, for example, bottles, vials, syringes, and test tubes. The containers can be formed from a variety of materials such as glass or plastic.

The articles of manufacture provided herein contain packaging materials. Examples of packaging materials include, but are not limited to, bottles, tubes, bags, containers, or bottles. A kit can include labels listing contents of the kit and/or instructions for use, and package inserts with instructions for use. A set of instructions can also be included. The instructions may be in physical or digital format (e.g., instructions that may be included in a pamphlet or stored in computer memory). The instructions may include instructions for implementing the methods provided herein, and/or preparing materials for use according to the methods provided herein.

The present disclosure will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments according to the invention. All patents, patent applications, and printed publications listed herein are incorporated herein by reference in their entirety.

EXAMPLES

Example 1

The present disclosure can be used as a companion assay for flow sequencing by synthesis. Flow sequencing by synthesis comprises repeated DNA extension cycles wherein individual species of nucleotides or nucleotides analogs are presented to a primer-template-polymerase complex which incorporates the nucleotide if complementary. The product of each flow is measured for each clonal population of templates, e.g., bead or colony. Quantifying the resulting incorporations entails unambiguously distinguishing signals, i.e., zero, one, or more sequential incorporations. Specifically, this requires a characteristic signal for each possible homopolymer incorporation on a clonal population in each flow. Random and unpredictable systematic variations in signal level can cause errors in quantifying the homopolymer length. Instrument and detection systematics can be calibrated and removed by monitoring instrument diagnostics and common-mode behavior across large numbers of colonies. However, sequence context-dependent signal is a special problem as it is different for every sequence.

For fluorescence measurements of dilute labeled nucleotides, sequence context can affect both the number of labeled analogs (variable tolerance for incorporating labeled analogs) as well as fluorescence of individual labeled analogs (e.g. quantum yield of dyes affected by local context of ±5 bases). In practice, with dye-terminator Sanger cycle sequencing, substantial systematic variations in signals have been identified for 3-base contexts. Reproducible fluorescent signal variations for 7 local contexts are shown in FIG. 1 for a Cy5 labeled dUTP.

Example 2

Figure 2A:
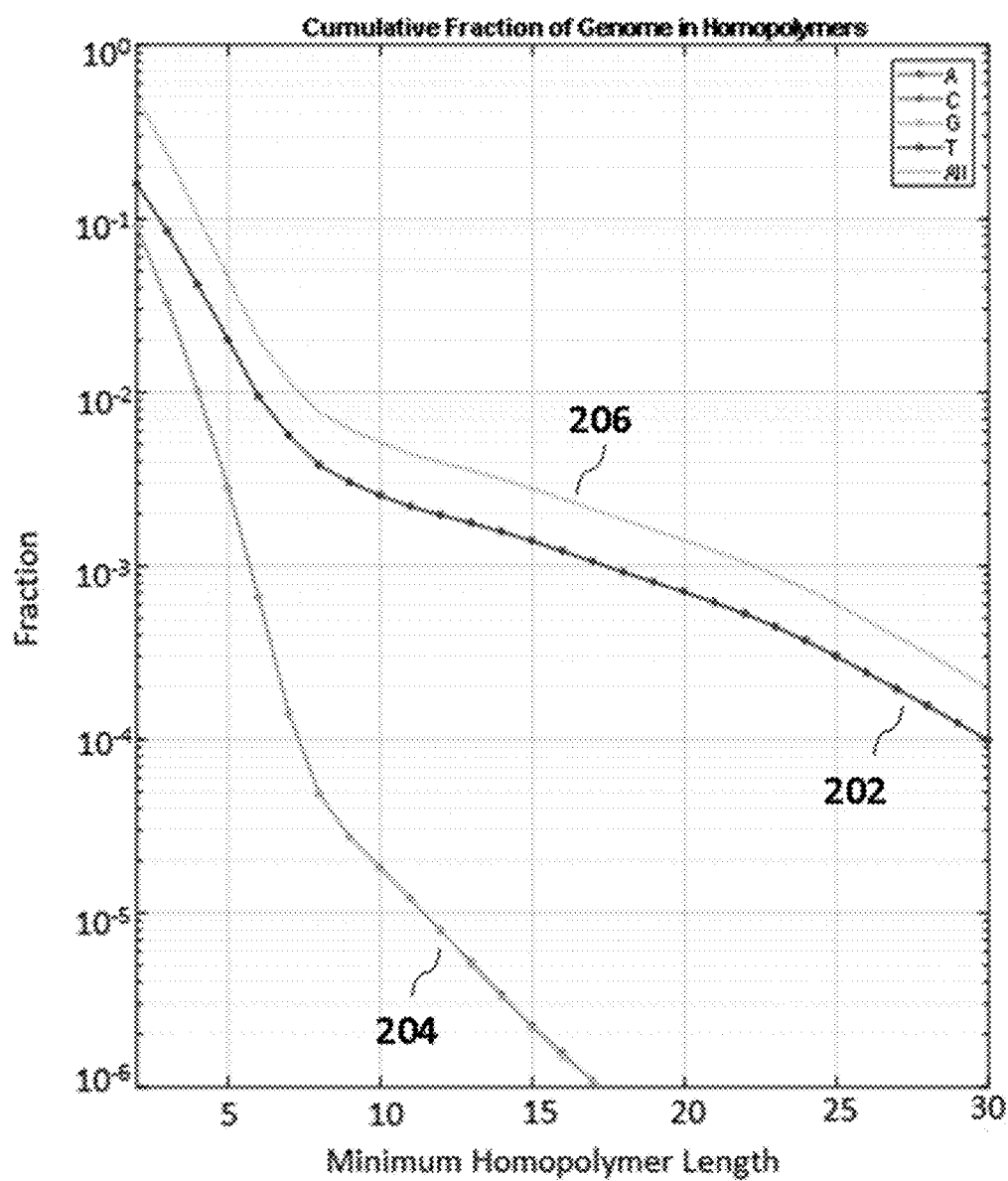
FIGS. 2A-B depict an example of homopolymer coverage of the human genome.
Figure 2B:
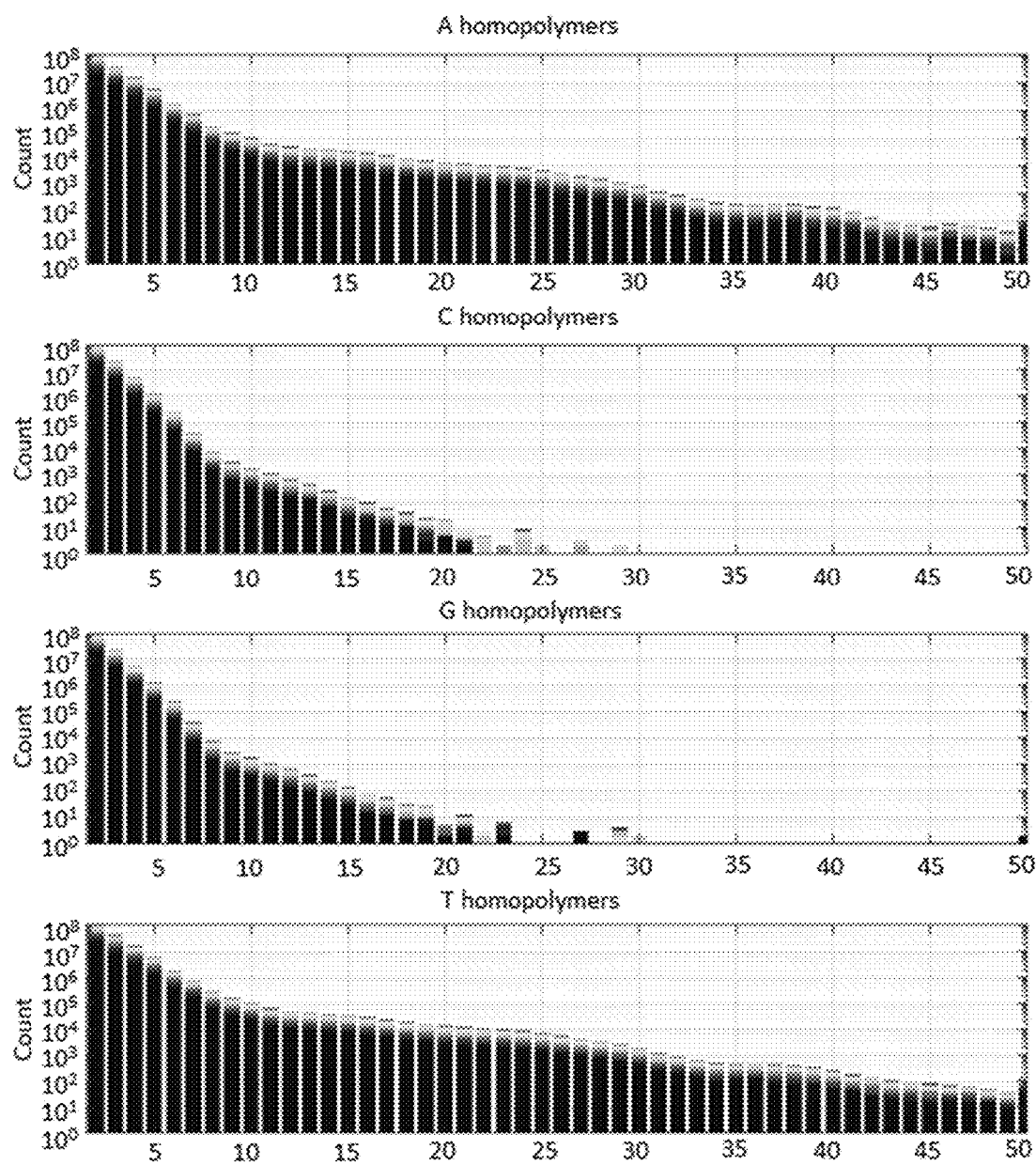

Quantifying long homopolymers can be difficult in that both systematic and random errors can compound to potentially produce large errors in length determination. However, large homopolymers are relatively rare in genomes, as illustrated by FIGS. 2A-B showing the homopolymer coverage of the human genome. FIGS. 2A-B show a fraction of human genome (GRCh38) comprising large homopolymers. The charts in FIGS. 2A-2B show the cumulative length weighted frequencies of homopolymers for each nucleotide species (e.g., 202 for T, 204 for C) and for all nucleotides together (e.g., 206 for cumulative). For example, 1% of this genome comprises homopolymers of length 7 and longer.

Example 3

Figure 3A:
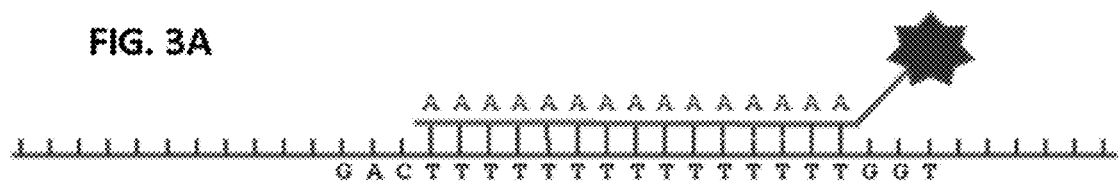
FIGS. 3A-3C depict homopolymer probes annealing to DNA templates.
Figure 3B:
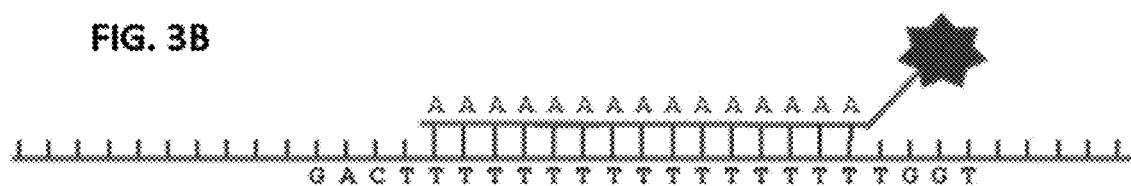
Figure 3C:
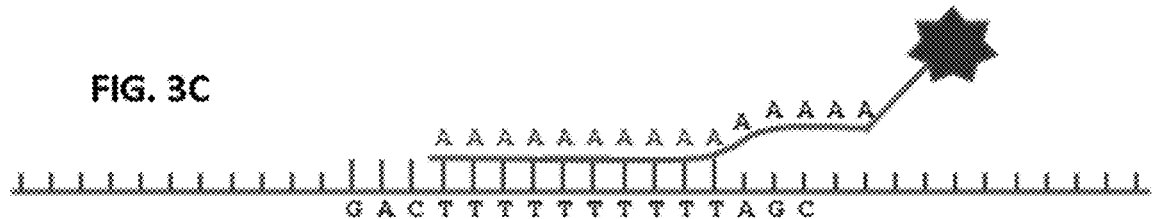

FIGS. 3A-C show an example of a homopolymer probe annealing to template DNA. In FIGS. 3A, 3B and 3C, respectively, the homopolymer is an exact match, shorter than, and longer than the template homopolymer. In this example, the probes are labeled with a fluorescent dye. In the example of FIG. 3C, binding properties, e.g., $T_m$, are modified by the degree of matching between the probe and the template. Presence of the probe at specific steps through a temperature sweep or concentration ramp of denaturant can be decoded to the homopolymer length over a range of lengths up to the probe homopolymer length.

Example 4

The methods in the present disclosure can become increasingly powerful for computing increasingly rare homopolymers, for example, those that are not likely to occur on a high fraction of reads, or more problematically, two or more times on a read. A stepped protocol delivering homopolymer probes with different length, for example, 5 nucleotides in length, 10 nucleotides in length, 15 nucleotides in length, 20 nucleotides in length can be used. Because longer homopolymers can be relatively rare, it is possible to simultaneously assess more than one species of nucleotide simultaneously to determine which species is present.

Figure 4:
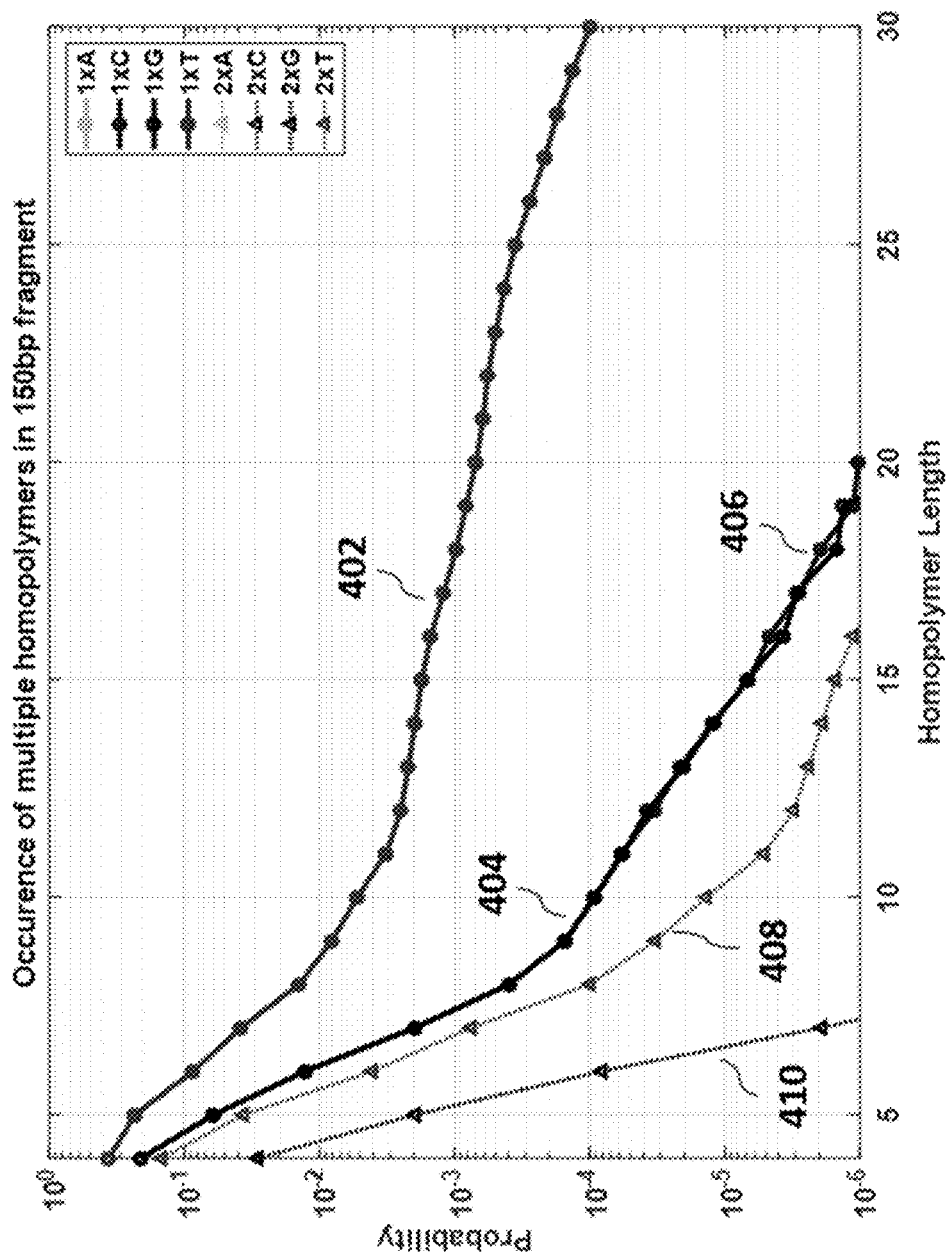
FIG. 4 depicts rate of occurrence of multiple homopolymers in a 150 bp fragment.

FIG. 4 shows the rate of occurrence of homopolymers of specified length and species to occur in a random 150 base pair (bp) fragment of GRCh38. FIG. 4 shows data sets for single occurrences and double occurrences for a species. For example, as seen by the single T repeat data points 402, the rate of occurrence for a single 10-base T repeat is about 0.5% and, as seen by the double T repeat data points 408, the rate of occurrence for a double 10-base T repeat is about 0.001%. FIG. 4 also shows single G repeat data points 404, single C repeat data points 406, and double C repeat data points 410. Generally, introduction of multiple non-complementary probes, each having a low probability (about <1%) of occurrence can have a very low rate probability (about <0.01%) of multiple labeling. Because long homopolymers can be relatively rare in the genome, statistically, pairs of non-complementary probes can be assayed together with little overlap on individual sequences. For example, two homopolymers of length 10 occur on a probability of about $10^{-5}$ of 150 bp fragments.

Example 5

The homopolymer probe can comprise a repeating region and, in some instances, a randomer region (e.g., a region with random sequences, as described elsewhere herein. In some instances, all introduced homopolymer probes may have the same length, which may be equal to the maximum length (N_max) of the homopolymer region that has to be reliably differentiated. By way of example, N_max=14. The sequencing system can reliably read a minimal length (N_min) of a homopolymer. By way of example, N_min=8. The homopolymer probe may comprise a homopolymer region (e.g., repetition region for a given base) with a repetition length of N_min, N_min+1, N_min+2 . . . N_max, and a randomer region for the remaining length to reach N_max. The randomer region may comprise randomized bases with the adjacent bases to the repetition length being one of the 3 other types of bases and the ones further out being any of the 4 types of bases; the homopolymer section may be flanked on both sides with randomers or just extended on one side with randomers to reach N_max. For example, where N_max is 14, and for a homopolymer probe with a homopolymer region length of 8 nucleotides, which is flanked on both sides with randomers, there can be 3×3×4⁴ possible sequences or 2,304 per base type. For 4 base types, the total can be 9,216 possible sequences. For a homopolymer probe with a homopolymer region length of 8 nucleotides, which is flanked on only one side with randomers, there can be 3×4⁵ possible sequences. As another example, for a homopolymer probe with a homopolymer region length of 9 nucleotides, which is flanked on both sides with randomers, there can be 3×3×4³ possible sequences or 576 per base type. For 4 base types, the total can be 2,304 possible sequences. As another example, for a homopolymer probe with a homopolymer region length of 13 nucleotides, flanked on one side with a randomer, there can be 3 possible sequences per base type.

These distinct homopolymer probes can have different labels such that they can be introduced simultaneously or separately in different batches. The difference can be in the fluorescence intensity, for example, via a different number of dyes, different types of dyes, or the same dyes having difference intensity in different configurations. Alternatively, the homopolymer probes can be introduced as a mixed population of labeled and un-labeled probes, and the different type/length may be differentiated by the proportion of labeled probes, and hence by the expected signal.

Figure 5:
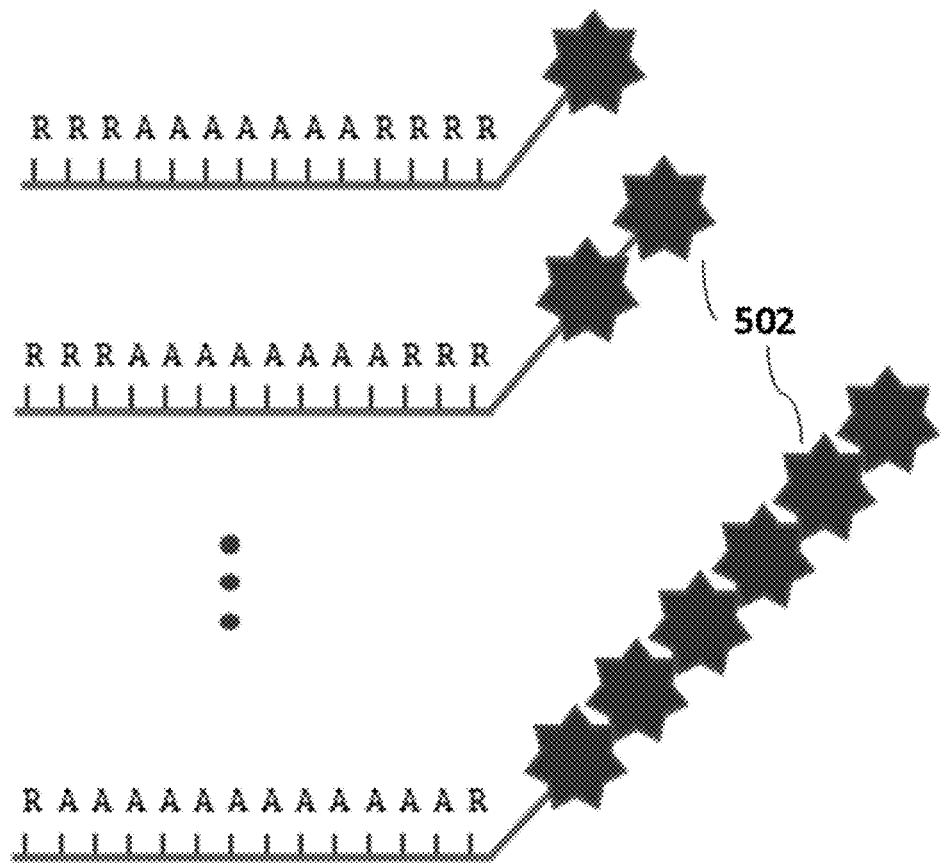
FIG. 5 depicts homopolymer probes comprising flanking randomers labeled with different numbers of dye molecules. R indicates a random nucleotide.

FIG. 5 shows an example of homopolymer probes with 14 nucleotides in length. In FIG. 5, the 'R' nucleotide indicates a randomer. A plurality of homopolymer probes is shown. The plurality of probes is differentiated by the number of dye molecules 502 on the respective probe in this example but may also include a fraction of dye labeled probes or dye molecule species. Each homopolymer probe has 14 nucleotides with differing lengths of homopolymer regions and randomer regions in each probe. The randomer adjacent to the homopolymer region may exclude the homopolymer species to improve specificity hybridization. For example, the randomer R adjacent to the homopolymer region 'A' may be selected from T, G, and C.

Example 6

In another example, the disclosed method can be used to detect even longer homopolymers. In this example, the homopolymer probes in the first flow will be at least one base longer than N_max and the random bases will be flanked on one side. After imaging, and without denaturing, another batch of homopolymer probes that have the randomers flanking the opposite side will be introduced in the second flow; essentially doubling the maximum homopolymer length that can be read without an extremely large number of randomer possibilities. Using a homopolymer probe of 14 nucleotides in length as an example, each run will read up to 13 (need at least one randomer per side) for a total readable length of 26. The second flow can be of a different dye that does not quench the first dye; or the dye can be connected on the randomer side so that the dyes are far apart and quenching is minimal, or the dyes can be attached to the oligonucleotide probes via cleavable linkers that can be cleaved between the two flows.

There may be several repeats: a first batch of homopolymer probes will be introduced to cover N_min to N_min+delta in a first run, after which the sample will be denatured, and a second batch of homopolymer probes will be introduced to cover N_min+delta to N_min+2×delta in a second run, and subsequently more runs will be performed until N_Max is reached; the runs may also have partial (or full) overlap in the homopolymer length ranges.

Example 7

Figure 6:
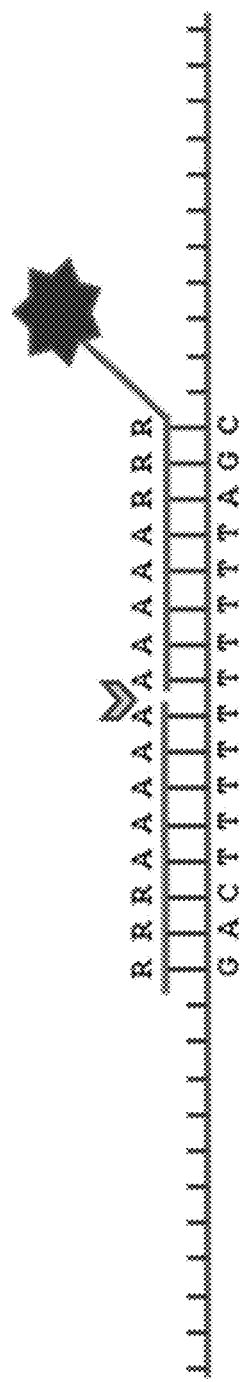
FIG. 6 depicts homopolymer bracketing probes annealed to a DNA template. The chevron indicates the ligation site.

In another example, homopolymer bracketing probes can be annealed to template DNA as in FIG. 6. After hybridizing, the probes can be ligated. Temperature or denaturant concentration can be raised to the level at which bracketing probes denature but the fully ligated probe of correct length remains. More than one labeled probe type may be introduced, each with a different homopolymer fragment length and a specific label. For example, the homopolymer bracketing probes can be labeled with different numbers of dye molecules or labeled with separate dye species, thereby providing a readout on multiple exact homopolymer lengths in an assay.

Example 8

Figure 7:
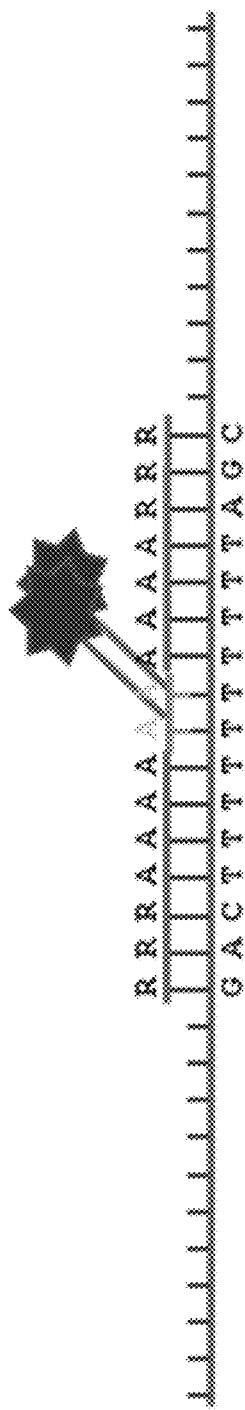
FIG. 7 depicts an example of annealed homopolymer bracketing probes followed by non-strand-displacing extension of labeled nucleotides.

In a related approach, two homopolymer bracketing probes can be annealed to a template DNA as in FIG. 7. A non-strand displacing extension can be accomplished with labeled nucleotides. Ligation may be performed to stabilize the hybridization. Fluorescent detection then provides a readout on the span of labeled bases indicating the homopolymer length. The labeled nucleotide analogs may be introduced together with a population of natural nucleotides to reduce the occurrence of nearby dye incorporations that may mutually interfere or quench.

Example 9

Figure 8:
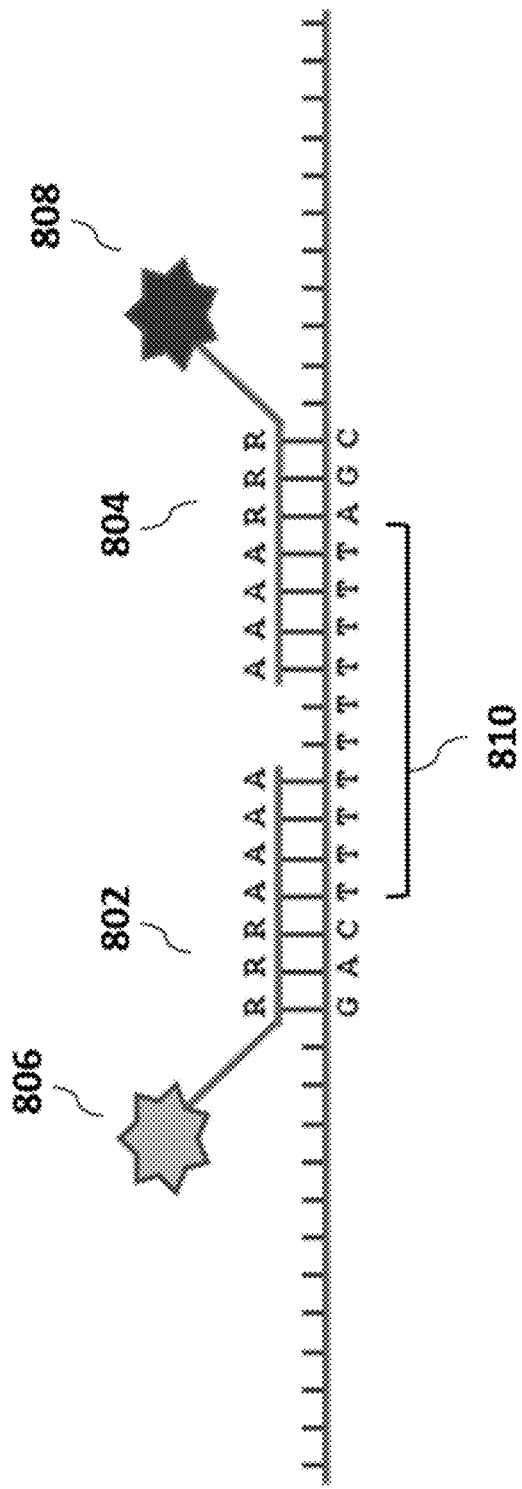
FIG. 8 depicts homopolymer bracketing probes labeled with FRET dye pair.

In another example, FIG. 8 shows labeled homopolymer bracketing probes 802, 804 that bind the flanks of a homopolymer region 810 in the target nucleic acid molecule. Homopolymer bracketing probes 802, 804 can be labeled with FRET dye pair 806, 808, respectively. For example, a first homopolymer bracketing probe 802 may be coupled to an acceptor dye 806, and a second homopolymer bracketing probe 804 may be coupled to a donor dye 808. The first homopolymer bracketing probe 802 may bind to a first end of the homopolymer region 810 in the target nucleic acid molecule. The second homopolymer bracketing probe 804 may bind to a second end (opposite the first end) of the homopolymer region 810. Displacement of the donor and acceptor dyes 806, 808 modulates the fluorescence signal giving a measure of homopolymer length. The homopolymer length can be inferred by the strength of the FRET interaction between donor and acceptor dyes on either probe.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

What is claimed is:

1. A method for identifying a sequence of a nucleic acid sample, comprising:
   (a) providing the nucleic acid sample comprising a first region and a second region, wherein the first region comprises a first homopolymer sequence, wherein the first homopolymer sequence has a first length, wherein the second region does not comprise the first homopolymer sequence;
   (b) hybridizing a probe comprising a second homopolymer sequence having a second length to the first homopolymer sequence of the first region, wherein:
      (i) a sequence of the first homopolymer sequence is complementary to a sequence of the second homopolymer sequence, and
      (ii) the probe yields an observable signal when the second homopolymer sequence is hybridized to the first homopolymer sequence;
   (c) detecting the observable signal;
   (d) processing an intensity or relative intensity of the observable signal to determine a match between the first homopolymer sequence and the second homopolymer sequence;
   (e) using the match determined in (d) to identify the first homopolymer sequence; and
   (f) using a sequence-by-synthesis reaction to determine a sequence of the second region.

2. The method of claim 1, wherein the first length of the first homopolymer sequence is shorter or longer than the second length of the second homopolymer sequence.

3. The method of claim 1, wherein the second length of the second homopolymer sequence is greater than 5 nucleotides.

4. The method of claim 1, wherein the observable signal is an optical signal, an electronic signal, or an electromagnetic signal.

5. The method of claim 4, wherein the optical signal comprises a fluorescent signal.

6. The method of claim 1, wherein the detecting of (c) comprises imaging.

7. The method of claim 1, further comprising generating a clonal copy of a target nucleic acid molecule wherein the nucleic acid sample is the clonal copy of the target nucleic acid molecule.

8. The method of claim 1, wherein the nucleic acid sample is attached to a bead or planar surface.

9. The method of claim 1, wherein the probe comprises at least one fluorescent label.

10. The method of claim 1, wherein the probe comprises a sequence of poly(dA), poly(dT), poly(dG), poly(dC), poly(rA), poly(U), poly(rG), or poly(rC).

11. The method of claim 1, wherein the probe further comprises a random sequence region comprising at least 1 nucleotide in length located at a 5' or 3' end of the probe.

12. The method of claim 1, wherein the probe comprises at least one modified locked nucleotide.

13. The method of claim 1, wherein the hybridizing of (b) is performed at a first temperature and the detecting of (c) is performed at a second temperature, wherein the first temperature is lower than the second temperature.

14. The method of claim 1, wherein the detecting of (c) is performed in a presence of a nucleic acid hybridization denaturant.

15. The method of claim 1, further comprising determining a sequence of the first region.

16. The method of claim 15, wherein the determining the sequence of the first region comprises synthesizing a complementary strand of the nucleic acid sample using the sequence-by-synthesis reaction, wherein the method further comprises removing a synthesized complementary strand of the nucleic acid sample.

17. The method of claim 1, wherein the probe further comprises a first bracketing probe and a second bracketing probe, wherein the first bracketing probe hybridizes to a first segment of the first homopolymer sequence and the second bracketing probe hybridizes to a second segment of the first homopolymer sequence.

18. The method of claim 17, further comprising ligating the first bracketing probe and the second bracketing probe.

19. The method of claim 17, wherein the first bracketing probe comprises a fluorescence resonance energy transfer (FRET) donor and the second bracketing probe comprises a FRET acceptor, thereby generating a FRET signal, wherein the first homopolymer sequence is identified at least partially based on a strength of the FRET signal.

20. The method of claim 1, further comprising repeating (b) and (c) at least once with at least one additional probe comprising an additional homopolymer sequence having a length different than the second length, to yield at least one additional observable signal from the at least one additional probe.

* * * * *